United States Patent
Fujita et al.

(10) Patent No.: US 9,710,907 B2
(45) Date of Patent: Jul. 18, 2017

(54) DIAGNOSIS SUPPORT SYSTEM USING PANORAMIC RADIOGRAPH AND DIAGNOSIS SUPPORT PROGRAM USING PANORAMIC RADIOGRAPH

(75) Inventors: Hiroshi Fujita, Gifu (JP); Takeshi Hara, Gifu (JP); Akitoshi Katsumata, Gifu (JP); Tatsuro Hayashi, Gifu (JP)

(73) Assignees: Gifu University, Gifu (JP); MEDIA CO., LTD., Tokyo (JP)

( * ) Notice: Subject to any disclaimer, the term of this patent is extended or adjusted under 35 U.S.C. 154(b) by 860 days.

(21) Appl. No.: 14/005,708

(22) PCT Filed: Mar. 13, 2012

(86) PCT No.: PCT/JP2012/056375
§ 371 (c)(1),
(2), (4) Date: Sep. 17, 2013

(87) PCT Pub. No.: WO2012/128121
PCT Pub. Date: Sep. 27, 2012

(65) Prior Publication Data
US 2014/0009573 A1    Jan. 9, 2014

(30) Foreign Application Priority Data

Mar. 18, 2011  (JP) ................................. 2011-060256
Dec. 22, 2011  (JP) ................................. 2011-280656

(51) Int. Cl.
*G06T 7/00*    (2017.01)
*A61B 6/14*    (2006.01)
(Continued)

(52) U.S. Cl.
CPC .............. *G06T 7/0012* (2013.01); *A61B 6/14* (2013.01); *A61B 6/5217* (2013.01);
(Continued)

(58) Field of Classification Search
None
See application file for complete search history.

(56) References Cited

U.S. PATENT DOCUMENTS

| | | | |
|---|---|---|---|
| 2006/0239532 | A1 | 10/2006 | Taguchi et al. |
| 2007/0286467 | A1 | 12/2007 | Asano et al. |

FOREIGN PATENT DOCUMENTS

| | | |
|---|---|---|
| JP | 2006-122211 | 5/2006 |
| JP | 3964795 | 8/2007 |

(Continued)

OTHER PUBLICATIONS

Hara T, Mori S, Kaneda T, Hayashi T, Katsumata A, and Fujita H, "Automated contralateral subtraction of dental panoramic radiographs for detecting abnormalities in paranasal sinus", Proc. of SPIE, 2011, vol. 7963, pp. 79632R-1-79632R-6; Cited in Specification; English text.

(Continued)

*Primary Examiner* — James M Anderson, II
(74) *Attorney, Agent, or Firm* — Rankin, Hill & Clark LLP

(57) ABSTRACT

A diagnosis support system includes a diagnosis support computer that includes a model data acquisition unit configured to obtain a plurality of mandible model data, a contour model creation unit configured to create contour model data from the mandible model data, a contour database storage unit configured to construct a contour model database from the contour model data, a diagnosis image data receiving unit configured to receive an input of diagnosis image data of an examinee, an edge extraction unit configured to extract edge data from the diagnosis image data, a similar model searching unit configured to search contour model data based on the edge data, a position judgment unit and an image quality judgment unit configured to judge an imaging position and an image quality (Continued)

based on imaging information, respectively, and a diagnosis support information provision unit configured to provide diagnosis support information based on provider information.

17 Claims, 15 Drawing Sheets

(51) Int. Cl.
*A61B 6/00* (2006.01)
*G06F 19/00* (2011.01)

(52) U.S. Cl.
CPC .......... *A61B 6/5241* (2013.01); *G06F 19/321* (2013.01); *G06F 19/345* (2013.01); *G06F 19/3437* (2013.01)

(56) References Cited

FOREIGN PATENT DOCUMENTS

| | | |
|---|---|---|
| JP | 2008-036068 | 2/2008 |
| JP | 2009-050632 | 3/2009 |
| WO | 2006/043523 | 4/2006 |

OTHER PUBLICATIONS

Guimond A, Meunier J, and Thirion JP, "Average Brain Models: A Convergence Study", Computer Vision and Image Understanding, 2000, vol. 77, pp. 192-210; Cited in Specification; English text.
Dinov ID, Mega MS, Thompson PM, Lee L, Woods RP, Holmes CJ, Summers DW, and Toga AW, "Analyzing Functional Brain Images in a Probabilistic Atlas; A Validation of Subvolume Thresholding", Journal of Computer Assisted Tomography, 2000, vol. 24(1), pp. 128-138; Cited in Specification; English text.
Park H, Bland PH, and Meyer CR, "Construction of an Abdominal Probabilistic Atlas and its Application in Segmentation", IEEE Transactions on Medical Imaging, 2003, vol. 22(4), pp. 483-492; Cited in Specification; English text.
Teruhiko Kitagawa, Xiangrong Zhou, Takeshi Hara, Hiroshi Fujita, Ryujiro Yokoyama, Hiroshi Kondo, Masayuki Kanematsu, and Hiroaki Noshi "Generation of a Probabilistic Liver Atlas and Its Application to Automated Liver Segmentation Method in Non-contrast X-Ray Torso CT Images" IEICE Transactions D, 2008, vol. J91-D(7), pp. 1837-1850; Cited in Specification; English abstract.
Blezek DJ and Miller JV, "Atlas stratification", Medical Image Analysis, 2007, vol. 11, pp. 443-457; Cited in Specification; English text.
Canny JF, "A Computational Approach to Edge Detection", IEEE Transaction on Pattern Analysis and Machine Intelligence, 1986, vol. PAMI-8(6), pp. 679-698; Cited in Specification; English text.
Zeyu Zheng and other three. "Quantitative Evaluation of Partial Shape Characteristics of Petal in Sacred Lotus Based on P-type Fourier Descriptors" Breeding Research, 2005, 7(3), pp. 133-142; Cited in Specification; English abstract.
Kirsh R, "Computer Determination of the Constituent Structure of Biological Images", Computers and Biomedical Research, 1971, vol. 4, pp. 315-328; Cited in Specification; English text.
Takuya Matsumoto and other eight, "Basic investigation on mandibular cortical thickness measurement in dental panoramic radiographs", JAMIT Annual Meeting 2010, Proceedings CD-ROM, 2010, pp. 1-6; Cited in Specification; English abstract.
Tatsuro Hayashi and other seven, "Development of Method of Automated Detection of Calcification in Carotid Artery Using Top-Hat Filter on Dental Panoramic Radiographs", The 15th Congress of Clinical Imaging for Oral and Maxillofacial Lesions 2010, O-S5-16, p. 47; Cited in Specification; English translation.
International Search Report dated Apr. 24, 2012 filed in PCT/JP2012/056375.
Extended European Search Report dated Jun. 9, 2015 issued in the corresponding EP Patent Application No. 12760788.5.
Allen P D et al.; "Detecting Reduced Bone Mineral Density From Dental Radiographs Using Statistical Shape Models", IEEE Transactions on Information Technology in Biomedicine, IEEE Service Center, Los Alamitos, CA, US, vol. 11, No. 6, Nov. 1, 2007 (Nov. 1, 2007), pp. 601-610, XP011345435, ISSN: 1089-7771, DOI: 10.1109/TITB.2006.888704.; Cited in Extended European Search Report.
Roberts M G et al., "Improving the detection of osteoporosis from dental radiographs using Active Appearance Models", Biomedical Imaging: From Nano to Macro, 2010 IEEE International Symposium on, IEEE, Piscataway, NJ, USA, Apr. 14, 2010 (Apr. 14, 2010), pp. 440-443, XP031693586, ISBN: 978-1-4244-4125-9.; Cited in Extended European Search Report.

FIG. 4
(a)
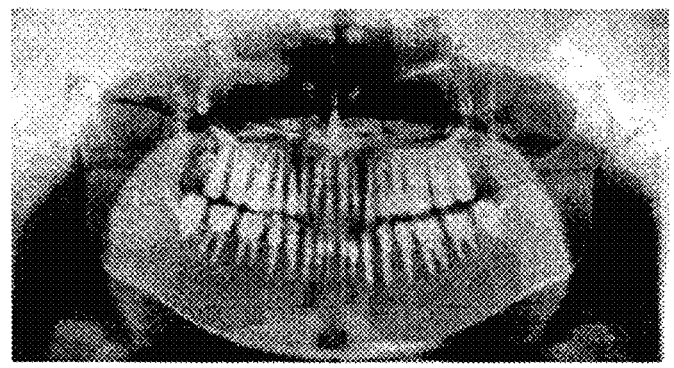
(b)
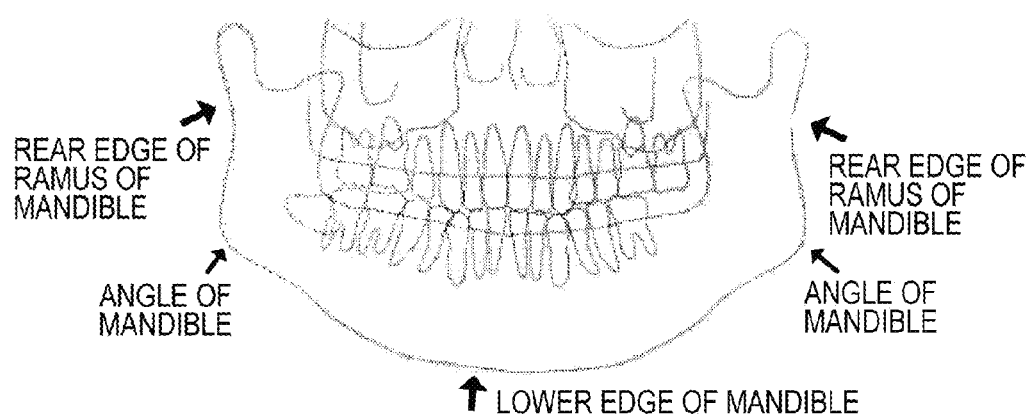
(c)
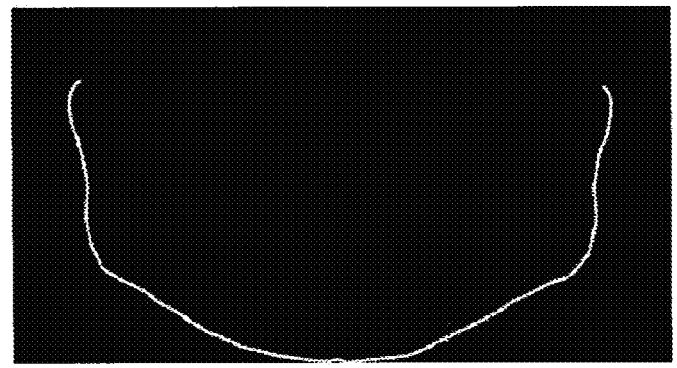

(a) STANDARD POSITION
(b) SHIFTED FORWARD BY 10 mm
(c) SHIFTED BACKWARD BY 10 mm
(d) SHIFTED RIGHTWARD BY 10 mm

FIG. 9
(a)
PANORAMIC IMAGE    CT IMAGE
(b)
● POSITION CORRESPONDING TO MENTAL FORAMEN
○ ANGLE OF MANDIBLE
AFTER APPLICATION OF ACTIVE CONTOUR MODEL → REGION OF INTEREST (RIGHT)   REGION OF INTEREST (LEFT)
FIG. 10
(a)
PANORAMIC IMAGE    CT IMAGE
(b)
PANORAMIC IMAGE → DIFFERENCE IMAGE
↓                ↓
RANGE IMAGE FROM CONTOUR → LIMIT RANGE OF DIFFERENCE IMAGE
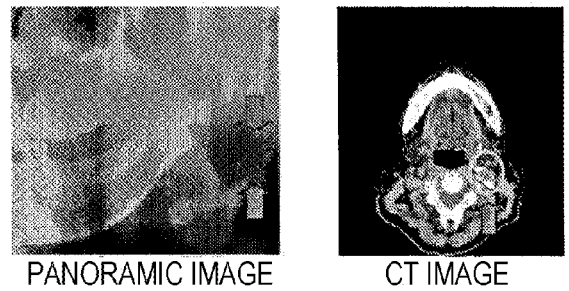
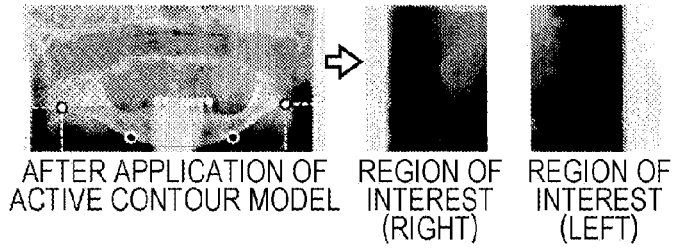
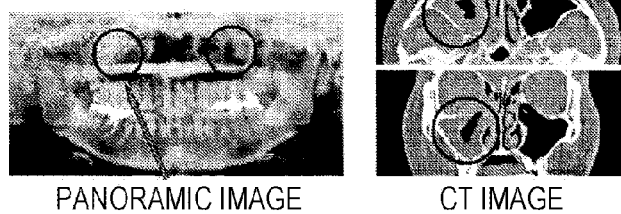
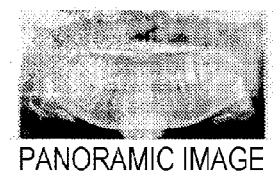
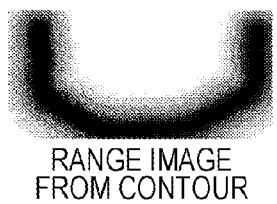

FIG. 14
(a)
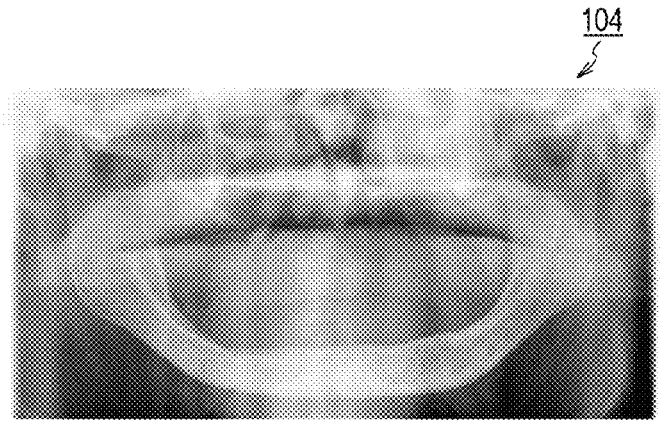
(b)
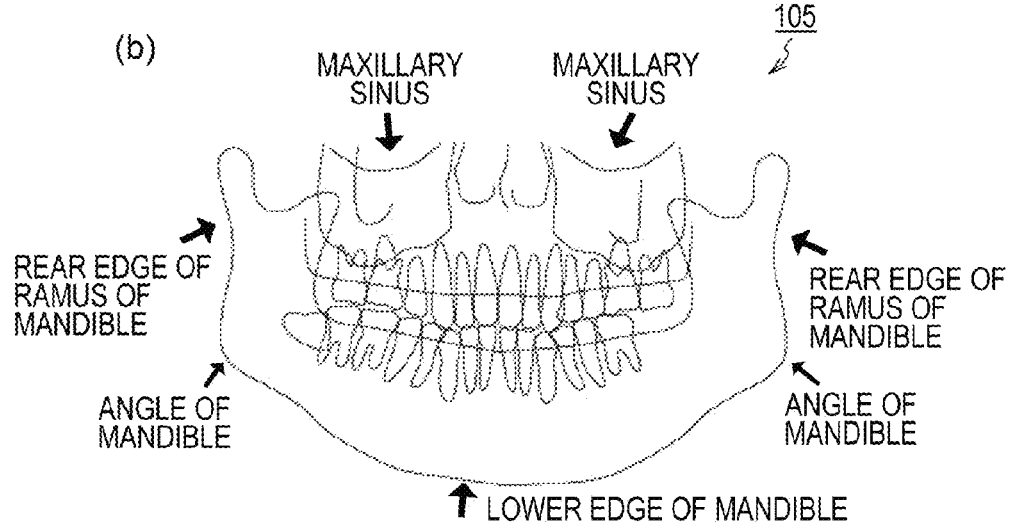
(c)
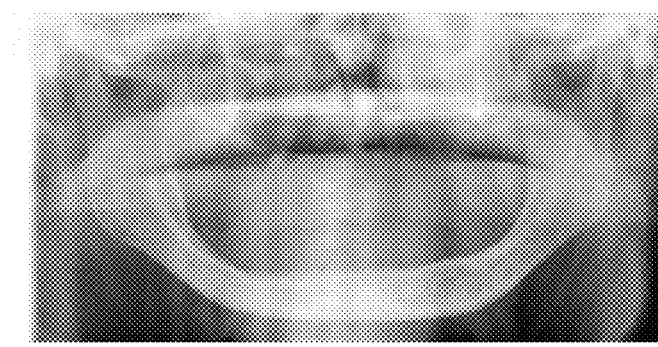

DIAGNOSIS SUPPORT SYSTEM USING PANORAMIC RADIOGRAPH AND DIAGNOSIS SUPPORT PROGRAM USING PANORAMIC RADIOGRAPH

TECHNICAL FIELD

The present invention relates to a diagnosis support system using a panoramic radiograph (hereinafter simply referred to as a diagnosis support system) and a diagnosis support program using the panoramic radiograph (hereinafter simply referred to as a diagnosis support program). Especially, the present invention relates to the diagnosis support system and the diagnosis support program that can determine whether radiographic imaging conditions are appropriate or not using a panoramic radiograph taken in odontotherapy and can provide information on diagnosis of a disease with a high risk of contraction (such as odontogenic maxillary sinusitis).

BACKGROUND ART

In odontotherapy, a region of the surface of a patient's jaw (including a maxilla, a mandible, a temporomandibular joint, and a maxillary sinus) may be imaged as one panoramic radiograph (hereinafter simply referred to as a panoramic image). The panoramic image is used as reference information beneficial for judging whether major diseases in the dental field are present or not and for determining, for example, other treatment policies. In particular, advancements in improved performance, downsizing, reduced cost, and similar improvement of an X-ray imaging apparatus and a digital information apparatus have been made recently. Accordingly, dental clinics that introduce an imaging apparatus for taking a digital panoramic image have been increasing.

A taken panoramic image is stored in, for example, an electronic medical recording system as image data together with basic information of a patient and medical information of the patient. The basic information includes, for example, a name, a date of birth, and a gender of the patient. The medical information includes, for example, treatment history up to the present and any other disease history. This facilitates checking a content of treatment of the patient after a set of treatment has been completed and grasping a healed state of the patient. The panoramic image may include information beneficial for diagnosing systemic diseases as well as diseases in the dental field. Accordingly, a technique for providing the beneficial information from the panoramic image including a mandible region has been developed (for example, see Patent document 1 to Patent document 3).

To describe more specifically, the taken panoramic image includes a pair of maxillary sinuses regions, which are one among the paranasal sinus pairs located on the right and left of the nose. The maxillary sinus has a bottom portion close to a tooth root portion. Therefore, bacteria causing an odontopathy, such as a decayed tooth and a periodontal disease, at a back tooth on a maxilla side may invade the maxillary sinus regions. This may result in incidence of "odontogenic maxillary sinusitis." This odontogenic maxillary sinusitis needs to be treated together with a tooth causing the odontogenic maxillary sinusitis, such as a decayed tooth, and therefore is generally treated at a dental clinic.

The panoramic image of a patient who has been affected by odontogenic maxillary sinusitis has the following features. That is, among a pair of maxillary sinuses at the right and left of a nose placing the nose as the center, one maxillary sinus region (the affected region) is radiopaque. Therefore, the affected region is mainly drawn in white or bright colors. The other maxillary sinus region (the normal region) is radiolucent. Therefore, the normal region is drawn in black or dark colors. That is, when the densities of the drawn right and left maxillary sinus regions are remarkably different in the panoramic image including both maxillary sinuses regions, this suggests high possibility of being affected by odontogenic maxillary sinusitis. Different from "odontogenic" maxillary sinusitis, in the case of "rhinogenous" maxillary sinusitis or "hematogenous" maxillary sinusitis, the distinctive observation (the difference in densities of the drawn right and left maxillary sinus regions) is less likely to be shown.

Meanwhile, the inventors of this application have developed an image processing system that emphasizes difference in density in the right and left maxillary sinus regions included in the taken panoramic image. The inventors of this application have also developed a system that creates a difference image of the right and left maxillary sinus regions (see Non-Patent Document 1). Use of this system allows a dentist or similar person to easily recognize density difference in the right and left maxillary sinus regions based on the contralateral subtraction image. As a result, since the dentist or similar person can judge possibility of whether a patient is affected by maxillary sinusitis and, for example, then examine the patient closely, early diagnosis and early treatment of odontogenic maxillary sinusitis are possible.

Here, technologies (atlases) for estimating the location where a specific target area is present from an obtained medical image based on prior information have been numerously developed. Disclosure examples of the technologies (atlases) are as follows. Namely, methods for creating an atlas for the brain region (see Non-Patent Document 2 and Non-Patent Document 3), methods for creating an atlas for the abdominal organs, whose morphological differences among individuals are greater than those of the brain region (see Non-Patent Document 4 and Non-Patent Document 5), and technology that estimates a degree of similarity between images using mutual information and create an atlas using only an image with high similarity (for example, Non-Patent Document 6) are disclosed. With these technologies, numerous attempts to create atlases in order to specify the target position from the medical image such as a panoramic image have been made. These techniques are effective techniques to judge possibility of odontogenic maxillary sinusitis and to specify a region of maxillary sinus.

SUMMARY OF THE INVENTION

Problems to be Solved by the Invention

However, to diagnose diseases in the dental field or to diagnose systemic diseases using the panoramic image, there is a possibility of causing the following problems. That is, the panoramic image needs to be taken accurately and strictly meeting radiographic imaging conditions. Therefore, an advanced imaging technique may be required for taking the panoramic image. More specifically, to take a panoramic image including a mandible region, three points as references are necessary, and the panoramic image need to be taken while always keeping the positions of these points. The three points are: the center ("median line") of the face of the subject to be imaged, a "Frankfurt plane" formed by connecting a right or left orbit and three points of the upper margin of an external auditory meatus, and a "tomographic zone" indicating a region imaged during tomography. Shifting of the three points during taking an image may cause a defect such as skewing and deformation of a finally-obtained panoramic image. The shifting also may vary an image quality in taking an image (for example, a position, intensity, density, and contrast of X-ray). A panoramic image taken under such inappropriate radiographic imaging conditions possibility causes insufficient judgment of, for example, a disease, overlooking of a disease, or suggestion of an incorrect disease. Therefore, if the panoramic image is not taken by an experienced oral maxillofacial radiology specialist or similar person, a disease may not be diagnosed.

Since a dentist who has knowledge of systemic diseases is not many, a disease inferred from the panoramic image taken at, for example, a dental clinic is mainly limited to diseases in the dental field. Therefore, even when the panoramic image has been taken under appropriate radiographic imaging conditions, a serious disease may be overlooked.

Diagnosing odontogenic maxillary sinusitis using a panoramic image may cause the following problems. That is, as described above, interpreting a case of odontogenic maxillary sinusitis from the panoramic image requires highly technical knowledge. Accurately diagnosing such case is difficult for a general doctor in private practice. Furthermore, use of the support system disclosed in Non-Patent Document 1 only emphasizes difference in density in regions of right and left maxillary sinuses by image process and does not indicate the density difference quantitatively. In view of this, a doctor or similar person who interprets the image judges the density difference based on subjective view, resulting in inaccurate diagnosis. Especially, the panoramic image is constructed as one panoramic image by compositely superimposing a plurality of structures. This significantly varies obtained panoramic images depending on, for example, imaging conditions. Furthermore, a technique for creating atlas is mainly targeting for a region such as a brain region or a region of abdominal organ, and the technique has not been attempted for a region including maxillary sinuses.

The present invention has been made considering the above circumstances. An object of the present invention is to judge radiographic imaging conditions when a panoramic image is taken and judge whether the panoramic image has been taken under appropriate radiographic imaging conditions or not. An object of the present invention is to infer various diseases including diseases in the dental field and systemic diseases other than the diseases in the dental field based on information obtained from the panoramic image. An object of the present invention is to provide a disease with a risk of contraction as diagnosis support information with, for example, a doctor or an examinee.

Solutions to the Problems

To solve the above-described problems, a diagnosis support system using a diagnosis support computer for analyzing a panoramic radiograph to provide diagnosis support information according to the present invention, includes: a model data acquisition unit configured to obtain a plurality of mandible model data by taking panoramic radiographs of a mandible region of a provider of mandible model based on each of a plurality of radiographic imaging conditions, the plurality of radiographic imaging conditions including an appropriate radiographic imaging condition and an inappropriate radiographic imaging condition; a contour model creation unit configured to extract a contour of the mandible from the obtained mandible model data to create contour model data; a contour database storage unit configured to store the created contour model data together with imaging information on an imaging position, an imaging posture, and an image quality, and provider information including an age, a gender, and a disease history of the provider of mandible model, the contour database storage unit constructing contour model database; a diagnosis image data receiving unit configured to receive an input of diagnosis image data, the diagnosis image data being obtained by taking a panoramic radiograph of a mandible region of an examinee who is a subject of diagnostic support; an edge extraction unit configured to extract edge data of the mandible from the received diagnosis image data; a similar model searching unit configured to collate the extracted edge data and a plurality of contour model data of the contour model database to search for the similar contour model data; a position judgment unit configured to judge an imaging position of the diagnosis image data and appropriateness of a position of an imaging posture based on the imaging information on the contour model data found by the similarity search; and an image quality judgment unit configured to judge degree of appropriateness of image quality including a density profile and a contrast of the diagnosis image data based on the imaging information of the contour model data found by the similarity search.

Here, the appropriate radiographic imaging conditions are conditions for adjustment as follows. That is, when taking the panoramic image of a mandible region, positioning of, for example, a median line to the center of the face of the provider of mandible model is minutely adjusted. An image quality (such as a density profile) is adjusted as well. In other words, the appropriate imaging conditions are conditions for taking a panoramic image under such adjustment. Accordingly, the panoramic image obtained under the appropriate imaging conditions has no skewing, deformation, and image quality error. That is, the appropriate imaging conditions are enough to, for example, infer a disease based on the panoramic image. Meanwhile, the inappropriate imaging conditions are conditions different from the appropriate imaging conditions. The inappropriate imaging conditions are conditions in which the panoramic image is taken at an incorrect position where the position or the orientation of the mandible region, which is a subject to be imaged, and an imaging posture of the provider of mandible model are out of appropriate range. Alternatively, the inappropriate imaging conditions are conditions in which the panoramic image is taken where ray dose is insufficient or too much or the image quality is inappropriate (such as a contrast error). The inappropriate imaging conditions include a plurality of conditions where imaging conditions are purposely changed from the appropriate imaging conditions to the same subject to be imaged. Then, a plurality of mandible model data of the same subject to be imaged is obtained under the inappropriate imaging conditions. Repeatedly obtaining the plurality of mandible model data from the plurality of providers of mandible model accumulates the plurality of mandible model data (a model data acquisition unit). Well-known panoramic radiography apparatuses, which have been introduced to, for example, dental clinics, are employed as imaging apparatuses for taking the panoramic image (mandible model data).

Meanwhile, a contour model creation unit extracts the contour of the mandible from the plurality of obtained mandible model data and creates contour model data based on image analysis. The contour model data can be created using a digital filter such as a Canny filter (see Non-Patent Document 7). Alternatively, the contour model data may be created by manually instructing the contour of the mandible model data. Furthermore, as disclosed in Non-Patent Document 8, the contour model data can be created by using P-type Fourier descriptors to convert the extracted contour shape into numerical values to define, and by performing a principal-components analysis with the coefficients of the Fourier descriptor as variates. The Fourier coefficients may be obtained by setting arbitrary conditions in advance for the created contour model data. An example of the arbitrary conditions that may be given is a condition whereby from eigenvectors defining principal components, the principal components whose scores are each 0 or a value that is two times the standard deviation are chosen, and the other principal-component scores all become 0. It is known that thus obtaining a Fourier coefficient and specifying the contour shape of mandible by inverse Fourier transformation (see Non-Patent Document 1).

Furthermore, the contour database storage unit stores the contour model data modeled by the above-described process in a contour model database. Especially, the contour model database stores imaging information and provider information together, thus the contour model database is constructed. The imaging information includes a position and a posture of the provider of mandible model, an image quality, the state of an imaging apparatus, or similar information when the contour model data is taken. The provider information includes information on the age, the gender, the disease history, and similar information of the provider of mandible model.

The edge extraction unit performs an image analysis process and extracts edge data of mandible. That is, the edge data of mandible is extracted from the diagnosis image data obtained by taking the panoramic image of the examinee who is the subject of diagnostic support. At this time, the image analysis process uses, for example, difference in number of pixels similarly to the contour detection of mandible in the contour model creation unit. At this time, the edge extraction unit may preliminary perform a mask process. Use of this mask process specifies the region of the mandible roughly, thus ensuring an efficient process speed and accurate edge data. To describe specifically, the edge process is to specify a position where a pixel of digital data is discontinuously changed. The edge process can apply a method such as a well-known Canny method.

Accordingly, the diagnosis support system according to the present invention performs the edge process on input diagnosis image data. The edge process compares the obtained edge data and the plurality of preliminary constructed contour model data of mandible. The contour model database is searched for the contour model data most similar to the obtained edge data. Then, based on the imaging information corresponding to the contour model data found by the similarity search, whether a position such as an imaging position and the image quality such as contrast is appropriate or not is judged. Thus, whether the diagnosis image data has been taken under the appropriate imaging conditions or not is judged. At this time, based on the imaging information, whether the contour model data has been taken under the appropriate imaging conditions or the inappropriate imaging conditions is judged. When the contour model data has been taken under the appropriate imaging conditions, the diagnosis image data is also judged to be taken under the appropriate imaging conditions. While the contour model data has been taken under the inappropriate imaging conditions, the diagnosis image data is also judged to be taken under the inappropriate imaging conditions.

Here, if the diagnosis image data is determined being taken under the inappropriate imaging conditions, the information is output and the process is terminated. In this case, a panoramic image needs to be taken again under the appropriate imaging conditions to obtain diagnosis image data again.

In addition to the above-described configuration, the diagnosis support system according to the present invention may further include a diagnosis support information provision unit configured to provide a disease with a risk of contraction as the diagnosis support information based on the provider information of the contour model data found by the similarity search, the diagnosis support information being provided with respect to the diagnosis image data judged to be taken under the appropriate imaging conditions by the position judgment unit and the image quality judgment unit.

Accordingly, in the diagnosis support system according to the present invention, the diagnosis image data judged as appropriate in all of, for example, an imaging position and image quality is used as follows. That is, based on the provider information corresponding to the contour model data, a disease with a high risk of contraction is inferred from the diagnosis image data. The inferred diseases are listed. Specifically, a disease with a risk is judged from treatment history and disease history included in the provider information of the provider of mandible model who provided the contour model data by similarity in mandible. This information is provided as diagnosis support information. Thus, the panoramic image of the mandible region is used for judging similarity with the plurality of contour model data included in the contour model database. Information on a disease with high possibility of being contracted for the examinee of the panoramic image is provided from the contour model database found by the similarity search. This processes judgment of appropriateness of the panoramic image and provision of information on morbidity risk in a sequence of flows.

In addition to the above-described configuration, the diagnosis support system according to the present invention may further include: a mandible contour detection unit configured to detect a contour of the mandible included in the diagnosis image data; and a disease detection unit configured to detect at least one disease of osteoporosis, calcification in carotid artery, and maxillary sinusitis based on the diagnosis contour data of the detected contour of the mandible.

Accordingly, the diagnosis support system according to the present invention further detects the contour of mandible from the diagnosis image data. At this time, the contour may be detected as follows. That is, the mandible of the contour model data already found by the similarity search is set as an initial contour. Using this initial contour, an active contour model to be converged to the edge of mandible is created based on the created edge data, thus detecting the contour. This allows detecting various diseases from the detected contour shape.

In addition to the above-described configuration, the diagnosis support system according to the present invention may further include: a range image creation unit configured to create a range image drawn by changing shading according to a distance from the edge of the mandible, using the extracted edge data; a contour restoration unit configured to restore a contour shape of the mandible from the contour model data; an average value calculation unit configured to superimpose restoration data of the restored contour shape and range image data of the created range image, the average value calculation unit calculating an average value on a contour; and a contour model specification unit configured to specify the contour model data with a contour shape of the mandible where the calculated average value is a minimum value, the contour model specification unit determining the specified contour model data as the similar contour model data.

Accordingly, the diagnosis support system according to the present invention creates a range image where shading is changed according to a distance from an edge portion based on the created edge data. The range image is collated with the contour shape of mandible restored from the contour model data. At this time, an average value of each contour is calculated. A process to specify the contour model data with the minimum calculated average value as a similar contour model is performed. This allows judging similarity based on difference between the range image and the contour shape of the restored contour model data.

In addition to the above-described configuration, in the diagnosis support system for providing information on possibility of odontogenic maxillary sinusitis by difference in density in the right and left maxillary sinus regions according to the present invention, the model data acquisition unit includes an image data acquisition unit configured to obtain panoramic image data of the panoramic radiograph where regions including the mandible region and the maxillary sinus region of the provider of mandible model have been taken as a subject to be imaged, the image data acquisition unit storing the panoramic image data, the diagnosis image data receiving unit includes a mandible/maxillary sinus diagnosis image data receiving unit configured to receive an input of mandible/maxillary sinus diagnosis image data of a test object image, the test object image being taken as the panoramic radiograph including regions of the mandible and the maxillary sinus of an examinee to be diagnosed, the edge extraction unit includes an edge data extraction unit configured to extract edge data candidate for a contour of the mandible from the received mandible/maxillary sinus diagnosis image data using a digital analysis technique, and the similar model searching unit includes a mandible similar model searching unit configured to collate the extracted edge data and a plurality of reference model data stored in the model database to search for similar reference model data with a contour shape of the mandible similar to the edge data. The diagnosis support computer includes: a reference model data creation unit configured to specify a contour shape of the mandible and a position of the maxillary sinus from the panoramic image data to create reference model data; a reference database construction unit configured to store a plurality of the created reference model data, the reference database construction unit constructing model database; an atlas creation unit configured to extract a region of a position of the maxillary sinus from the similar reference model data found by the similarity search to create an atlas of the maxillary sinus; a maxillary sinus image extraction unit configured to extract a maxillary sinus image corresponding to a region of the maxillary sinus from the mandible/maxillary sinus diagnosis image data based on the atlas; a feature quantity calculation unit configured to calculate each of feature quantities of the extracted right and left pair of maxillary sinus image; and a risk rate estimation unit configured to estimate a risk rate associated with a contraction of odontogenic maxillary sinusitis by the examinee, the mandible/maxillary sinus diagnosis image data being obtained from the examinee, the risk rate being estimated from feature quantity data associated with the calculated feature quantities.

Here, the image data acquisition unit electrically obtains and stores the panoramic image as panoramic image data. The panoramic images are taken setting a region including the mandible and the maxillary sinuses of the plurality of providers of mandible model (living bodies) as a subject to be imaged using a panoramic radiography apparatus. The panoramic image data is storable as an image file in a storage unit such as a hard disk drive and a non-volatile memory. The panoramic image data may include an image taken regions of mandible and maxillary sinuses of a head phantom for radiographic imaging constructed by artificial bones as a subject to be imaged. This accumulates panoramic image data of a plurality of subjects to be imaged.

Meanwhile, the reference model data creation unit creates reference model data. Here, the reference model data includes the contour shape of mandible and positions of maxillary sinuses specified from the obtained panoramic image data. The reference model data creation unit, for example, may extract the contour shape applying an image analysis technique using a digital filter such as a Canny filter. Alternatively, the reference model data creation unit may specify the contour shape of mandible and the positions of maxillary sinuses by manually specifying the positions along the contour part included in the panoramic image data. Furthermore, the reference model data creation unit may automatically specify the contour shape of mandible and the positions of maxillary sinuses applying an image analysis technique to the regions of the maxillary sinuses as well. Alternatively, the reference model data creation unit may manually specify the region by a doctor or similar person with advanced interpretation techniques. The reference model data creation unit specifies information on the contour shape of mandible and information on the positions of maxillary sinuses correlatively with each other. The contour shape of mandible (lower edge portion+rear edge portion) drawn to the panoramic image is less affected by presence/absence of tooth, opening/closing state of mouth, and ghost reflections from obstructive shadows. Therefore, the contour shape of mandible can be used as a reference position in the panoramic image. Determining positional relationship of the maxillary sinus relative to the contour shape of mandible allows correctly grasping the positions of maxillary sinuses. The positions of maxillary sinuses, for example, may be specified by being extracted in precise shape according to the shape of regions of maxillary sinuses. Alternatively, the positions of maxillary sinuses may be specified by specifying the regions of maxillary sinuses in a simple drawing such as a rectangle. Accordingly, the reference model data includes information on the contour shape of mandible and information on the position, size, or similar specification of the regions of maxillary sinuses specified by the positional relationship relative to the contour shape. Each of created reference model data is accumulated, thus a model database is constructed. The constructed model database is stored in the storage unit.

Meanwhile, the edge data extraction unit performs an image analysis process on mandible/maxillary sinus diagnosis image data and extracts edge data candidate for the contour of mandible. The mandible/maxillary sinus diagnosis image data is obtained by taking a panoramic image (a test object image) of a region including the mandible and the maxillary sinus of the examinee to be diagnosed. The mandible/maxillary sinus diagnosis image data receiving unit receives an input of the obtained mandible/maxillary sinus diagnosis image data. The edge data obtained by the edge data extraction unit is collated with the reference model data including data on the plurality of contour shapes of mandibles stored in the preliminary constructed model database. The reference model data of the contour shape similar to the edge data (similar reference model data) is searched.

Furthermore, the atlas creation unit specifies the regions of maxillary sinuses based on the similar reference model data found by the similarity search and then creates the region as atlas. The maxillary sinus image extraction unit superimposes the created atlas and the diagnosis image data, matching the contour shapes of mandibles. The region of the diagnosis image data corresponding to the atlas (a region of interest) is extracted as a maxillary sinus image. Here, the pair of maxillary sinuses is present at the right and left of a face placing a nose as the center. Accordingly, the created atlas and the extracted maxillary sinus image are also left-and-right pair. This specifies the regions of maxillary sinuses based on the contour shape of mandible. The maxillary sinus image is automatically extracted from the diagnosis image data. Meanwhile, the feature quantity calculation unit quantitatively obtains density difference of the obtained maxillary sinus image based on various parameters. This allows obtaining a pixel value of the maxillary sinus image (for example, a mean value and a median), the size of the region of maxillary sinus, or similar specification. Based on the value, a risk rate can be estimated according to the difference in feature quantities of the right and left maxillary sinus image.

Accordingly, the diagnosis support system according to the present invention performs an edge process on the received mandible/maxillary sinus diagnosis image data. Based on the obtained edge data, the preliminary constructed model database is searched for the most similar reference model data. Then, the atlases for the regions of maxillary sinuses are created from the similar reference model data found by the similarity search. The atlas is superimposed with the diagnosis image data so as to match the mandibles, and the maxillary sinus image is extracted. Next, the feature quantities are calculated, and the risk rate is estimated.

In addition to the above-described configuration, the diagnosis support system according to the present invention claim may further include: a smoothing unit configured to perform a smoothing process on the mandible/maxillary sinus diagnosis image data using a Gaussian filter, the smoothing unit removing noise included in the diagnosis image data; a mask unit configured to preliminary perform a mask process on a position where presence of the mandible is expected in the obtained smoothed data; a gradient direction prediction unit configured to predict a gradient direction of an edge constituting a contour shape of the mandible in the obtained mask data; a gradient intensity calculation unit configured to calculate gradient and intensity of the edge of the obtained gradient prediction data using a Kirsch method; a thinning unit configured to thin the edge of the calculated intensity data by non-maximum suppression process; and a threshold process unit configured to perform a hysteresis threshold process on the obtained thinned data to extract the edge data.

Accordingly, the diagnosis support system according to the present invention uses a method combining the Canny method and the Kirsch method to extract the edge data of mandible form the diagnosis image data. Especially, a gradient at an edge of contour becomes predicable by smoothing process and mask process. Then, the gradient and the intensity are calculated employing the Kirsch method. Thus, accuracy of the extracted edge data becomes high.

In addition to the above-described configuration, the diagnosis support system according to the present invention may further include: a distance transform unit configured to create a distance transform image from the edge data extracted from the diagnosis image data; an affine transformation unit configured to perform an affine transformation process on the reference model data stored in the model database; and a similarity degree estimation unit configured to estimate a degree of similarity between distance transform image data of the distance transform image and the reference model data after an affine transformation process, and extract similar reference model.

Accordingly, the diagnosis support system according to the present invention first creates a distance transform image from the extracted edge data. Next, affine transformation is performed on the plurality of mandible/maxillary sinus model data stored in the model database. Then, the affine-transformed data and the created distance transform image data are estimated for a degree of similarity. Here, the affine transformation is to summarize, for example, zoom, rotation, and parallel movement of an image and to transform data using matrix. This estimates the degree of similarity between the affine-transformed mandible/maxillary sinus model data and the distance transform image data. At this time, only the model with the highest degree of similarity may be output. Alternatively, a plurality of model data may be output in order of higher degree of similarity. Alternatively, threshold for the degree of similarity may be preliminary determined, and model data within the threshold may be output.

A diagnosis support program according to the present invention may allow a diagnosis support computer to function as: a model data acquisition unit configured to obtain a plurality of mandible model data by taking panoramic radiographs of a mandible region of a provider of mandible model based on each of a plurality of radiographic imaging conditions, the plurality of radiographic imaging conditions including an appropriate radiographic imaging condition and an inappropriate radiographic imaging condition; a contour model creation unit configured to extract a contour of the mandible from the obtained mandible model data to create contour model data; a contour database storage unit configured to store the created contour model data together with imaging information on an imaging position, an imaging posture, and an image quality, and provider information including an age, a gender, and a disease history of the provider of mandible model, the contour database storage unit constructing contour model database; a diagnosis image data receiving unit configured to receive an input of diagnosis image data, the diagnosis image data being obtained by taking a panoramic radiograph of a mandible region of an examinee who is a subject of diagnostic support; an edge extraction unit configured to extract edge data of the mandible from the received diagnosis image data; a similar model searching unit configured to collate the extracted edge data and a plurality of contour model data of the contour model database to search for the similar contour model data; a position judgment unit configured to judge an imaging position of the diagnosis image data and appropriateness of a position of an imaging posture based on the imaging information on the contour model data found by the similarity search; and an image quality judgment unit configured to judge degree of appropriateness of image quality including a density profile and a contrast of the diagnosis image data based on the imaging information of the contour model data found by the similarity search. Alternatively, the diagnosis support program according to the present invention may further function the diagnosis support computer as the edge data extraction unit. The edge data extraction unit includes: a smoothing unit configured to perform a smoothing process on the mandible/maxillary sinus diagnosis image data to remove noise included in the diagnosis image data using a "Gaussian filter", a mask unit configured to preliminary perform a mask process on the obtained smoothed data at a position where presence of the mandible is expected, a gradient direction prediction unit configured to predict a gradient direction of an edge constituting a contour shape of the mandible in the obtained mask data, a gradient intensity calculation unit configured to calculate gradient and intensity of the edge of the obtained gradient prediction data using a Kirsch method, a thinning unit configured to thin the edge of the calculated intensity data by non-maximum suppression process, and a threshold process unit configured to perform a hysteresis threshold process on the obtained thinned data and extracts the edge data. Alternatively, the diagnosis support program according to the present invention may further function the diagnosis support computer as the mandible similar model searching unit. The mandible similar model searching unit includes: a distance transform unit configured to create a distance transform image from the edge data extracted from the diagnosis image data, an affine transformation unit configured to perform an affine transformation process on the reference model data stored in the model database, a similarity degree estimation unit configured to estimate a degree of similarity of the distance transform image data of the distance transform image and the reference model data after an affine transformation process and extract a similar reference model.

Accordingly, the diagnosis support program according to the present invention allows providing the following operational effects with the diagnosis support computer. That is, executing the program allows operating the diagnosis support computer in the above-described diagnosis support system. The diagnosis support program according to the present invention allows the diagnosis support computer to provide information on degree of appropriateness of radiographic imaging of a taken and input panoramic radiograph and information to infer odontogenic maxillary sinusitis with a high risk of contraction from the obtained diagnosis image data.

Effects of the Invention

As effect of the present invention, a degree of similarity of mandible shape can be judged from a contour model database. Degree of appropriateness of radiographic imaging conditions can be judged from imaging information of similar contour model data. Furthermore, based on provider information, information on a disease with a high risk of contraction can be provided. As effect of the present invention, feature quantities of right and left maxillary sinus image created from extracted similar reference model data as atlas of maxillary sinuses and then specified can be calculated. Comparing these data with one another can provide information on possibility (a risk rate) of odontogenic maxillary sinusitis. These effects allow reducing workload of, for example, a doctor who analyzes an image and providing beneficial diagnosis support information using a panoramic image.

BRIEF DESCRIPTION OF THE DRAWINGS

FIG. 4(a) is a panoramic radiograph, FIG. 4(b) is a schematic view of a mandible, and FIG. 4(c) is an explanatory view illustrating contour model data.

FIG. 9(a) is an explanatory view illustrating an exemplary calcification in carotid artery, and FIG. 9(b) is an explanatory view illustrating an exemplary region of interest setting for detecting the calcification in carotid artery.

FIG. 10(a) is an explanatory view illustrating an exemplary radiopacity of a maxillary sinus, and FIG. 10(b) is an explanatory view illustrating an exemplary region of interest setting of the maxillary sinus.

FIG. 14(a) is a test object image, FIG. 14(b) is a schematic view of a structure of human body, and FIG. 14(c) is an explanatory view illustrating a smoothed image.

DESCRIPTION OF EMBODIMENTS

Figure 1:
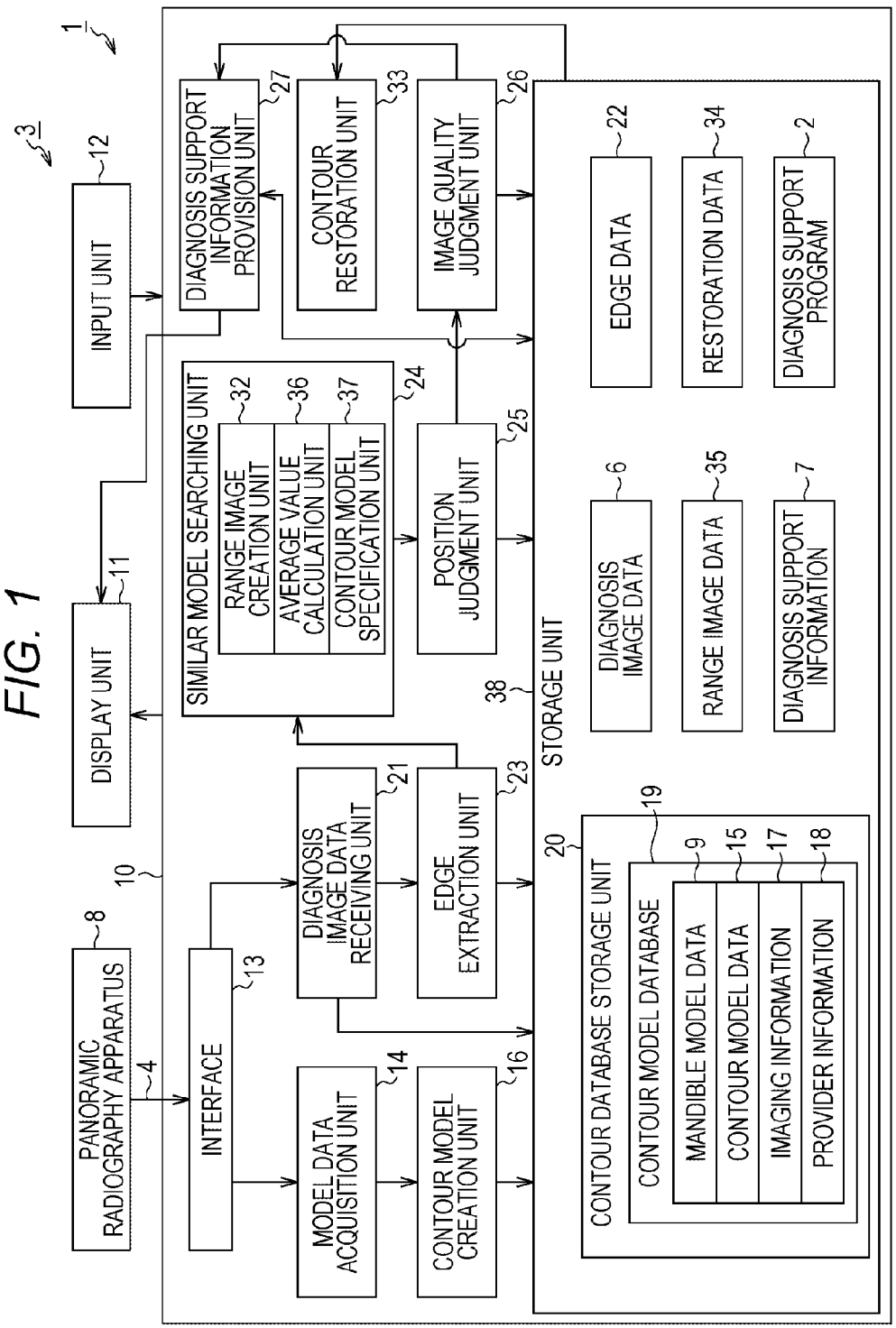
FIG. 1 is a block diagram illustrating a functional configuration of a diagnosis support computer included in a diagnosis support system according to a first embodiment.

The following mainly describes a diagnosis support system 1 according to the first embodiment of the present invention and a diagnosis support program 2 for the diagnosis support system 1 based on FIG. 1 to FIG. 10. The diagnosis support system 1 according to this embodiment is mainly constituted by a diagnosis support computer 3. As shown in FIG. 1 and similar drawing, the diagnosis support computer 3 receives an input of diagnosis image data 6 of a taken panoramic image 4, analyzes the image, and judges whether radiographic imaging conditions or similar condition are appropriate or not. Thus, the diagnosis support system 1 can provide diagnosis support information 7 for supporting diagnosis by a doctor or similar person to the doctor or similar person. Here, a panoramic radiography apparatus 8 (hereinafter referred to as an imaging apparatus 8) takes a panoramic image 4 of a mandible region of a provider of mandible model or a mandible region of an examinee to be diagnosed. The imaging apparatus 8 is directly coupled to the diagnosis support computer 3 in a first embodiment. The panoramic image 4 taken by the imaging apparatus 8 can be directly input to the diagnosis support computer 3 as computerized mandible model data 9 or the diagnosis image data 6. The diagnosis support program 2 according to the present invention has been installed on the diagnosis support computer 3. Therefore, starting the diagnosis support program allows the diagnosis support computer 3 to function such that the diagnosis support computer 3 achieves each operational effect of the diagnosis support system 1 according to the present invention.

The diagnosis support computer 3 may be constructed applying a commercially available personal computer. The diagnosis support computer 3 mainly includes a casing-shaped computer main body 10, a display unit 11 such as a liquid crystal display, and an input unit 12 such as a keyboard and a computer mouse. The display unit 11 is coupled to the computer main body 10 and can display and output various information and data. The input unit 12 performs various operations on the computer main body 10. The diagnosis support computer 3 may be a so-called notebook computer.

The diagnosis support computer 3 is coupled to the above-described imaging apparatus 8 via an interface 13 for image data input. The computer main body 10 internally includes, similarly to ordinary personal computers, various hardware. The hardware includes, for example, a Central Processing Unit (CPU), which performs various processes, a memory for storing temporary data, a hard disk drive as a storage unit for storing various information and data, and a network interface for adding a network function such as the Internet (some parts are not shown). The imaging apparatus 8 needs not to be directly coupled to the computer main body 10 as described above. The computer main body 10 may receive inputs of the mandible model data 9 and the diagnosis image data 6 obtained by the imaging apparatus 8 via a well-known storage medium or a network line.

As shown in FIG. 1 and similar drawing, the diagnosis support computer 3 of the diagnosis support system 1 according to the first embodiment includes a model data acquisition unit 14, a contour model creation unit 16, a contour database storage unit 20, a diagnosis image data receiving unit 21, an edge extraction unit 23, a similar model searching unit 24, a position judgment unit 25, an image quality judgment unit 26, and a diagnosis support information provision unit 27 as the functional configuration. The model data acquisition unit 14 acquires the mandible model data 9 obtained by computerizing the panoramic image 4. The panoramic image 4 with a subject of mandible region of a provider of mandible model (not shown) is taken under a plurality of radiographic imaging conditions including at least one appropriate imaging condition using the imaging apparatus 8. The contour model creation unit 16 extracts a contour of mandible from the obtained mandible model data 9 and creates contour model data 15. The contour database storage unit 20 stores the imaging information 17 and the provider information 18 together with the created contour model data 15. The imaging information 17 includes information on an imaging position and an imaging posture when the panoramic image 4, which will be a base of the mandible model data 9, is taken, an image quality of the panoramic image 4, and similar information. The provider information 18 includes information on disease history of the provider of mandible model and similar information. The contour database storage unit 20 constructs a contour model database 19. The diagnosis image data receiving unit 21 receives an input of the diagnosis image data 6 obtained from the panoramic image 4 of the examinee who is the subject of diagnostic support taken by the imaging apparatus 8. The edge extraction unit 23 extracts edge data 22 of mandible from the received diagnosis image data 6. The similar model searching unit 24 collates the edge data 22 and the contour model data 15 stored in the contour model database 19 with one another and searches for similar contour model data. The position judgment unit 25 judges whether the imaging position of the diagnosis image data 6 or similar condition is appropriate or not based on the imaging information 17 of the contour model data 15 found by the similarity search. The image quality judgment unit 26 judges whether the image quality of the diagnosis image data 6 is appropriate or not based on the imaging information 17. The diagnosis support information provision unit 27 infers a disease with a risk of contraction from the diagnosis image data 6 judged as appropriate in position and image quality based on, for example, disease history of the provider of mandible model included in the provider information 18 corresponding to the contour model data 15 found by the similarity search and provides the inference result as the diagnosis support information 7.

The similar model searching unit 24 further includes a range image creation unit 32, a contour restoration unit 33, an average value calculation unit 36, and a contour model specification unit 37. The similar model searching unit 24 creates a range image 5. The range image 5 is drawn using the extracted edge data 22 such that shading changes corresponding to a distance from an edge 31 of the mandible. The contour restoration unit 33 restores the contour shape of the mandible from the contour model data 15. The average value calculation unit 36 superimposes restoration data 34 of the restored contour shape and range image data 35 of the created range image 5, and calculates an average value. The contour model specification unit 37 specifies the contour model data 15 where the calculated average value is the minimum value, and then judges this contour model data 15 similar to the diagnosis image data 6.

Next, a concrete example of providing the diagnosis support information 7 by the diagnosis support system 1 according to the first embodiment will be described based on the flowcharts in FIG. 2 and FIG. 3 and similar drawing. The diagnosis support system 1 according to this embodiment performs a plurality of processes. Exemplary processes include a process that stores the contour model data 15 of similarity search target and to construct the contour model database 19 and a process that provides the diagnosis support information 7 on a disease with a high risk of contraction from the diagnosis image data 6 of the examinee using the constructed contour model database 19.

Now, the construct process of the contour model database 19 will be described. First, the panoramic images 4 where a plurality of mandible regions of providers of mandible models are subjects to be imaged are taken using the imaging apparatus 8 (Step S1, see FIG. 4(a)). FIG. 4(b) is a schematic view of a general mandible. As seen from this drawing, the contour of mandible (namely, the lower edge portion and the rear edge portion), can be stably image-drawn. This is probably because that the contour of mandible is less affected by presence/absence of tooth, opening/closing state of mouth, or ghost reflections from obstructive shadows. Accordingly, the panoramic image 4 of the mandible region is employed here.

The contour of mandible is extracted from the mandible model data 9 of the taken panoramic image 4 (Step S2). Specifically, using the above-described image analysis technique with Canny filter, the contour of mandible is extracted. This technique performs a process that specifies a portion of discontinuous pixel values of digital data and detects the contour part. Then, the extracted contour shape is formulated (modeled) (Step S3). Based on the modeled contour shape, the contour model data 15 of the contour shape of mandible is created from the panoramic image 4 (see FIG. 4(c)). A method using a P-type Fourier descriptor disclosed in the above-described Non-Patent document 8 is applicable to modeling of the contour shape. Details of these processes are omitted.

Here, in Step S1, the panoramic image 4 is taken under appropriate radiographic imaging conditions and a plurality of inappropriate radiographic imaging conditions. Here, the appropriate imaging conditions are conditions where an imaging position when the mandible region is a subject to be imaged, a posture of the provider of mandible model, and an image quality of the panoramic image (for example, a density and a contrast) are preliminarily specified within appropriate ranges. The inappropriate imaging conditions are conditions where the appropriate imaging conditions are purposely changed outside the appropriate ranges. As shown in FIG. 5(a) to FIG. 5(d), for example, the imaging position is changed to frontward 10 mm, backward 10 mm, and rightward 10 mm with respect to the appropriate imaging condition (FIG. 5(a)). Under these conditions, each panoramic image 4 is taken. Next, the contours of the panoramic images 4 taken under different conditions are extracted, thus each contour model data 15 is created. These processes obtain the plurality of panoramic images 4, mandible model data 9, and contour model data 15 as information for one subject to be imaged. Performing such processes on the plurality of providers of mandible model constructs the contour model database 19 (Step S4). The provider of mandible model usually means a living body (human). However, the plurality of panoramic images 4 may be taken using, for example, a head phantom made by artificial bones for radiographic imaging as a part of the providers of mandible models.

At this imaging, the contour model data 15 is stored together with the imaging information 17 and the provider information 18 to construct the contour model database 19. The imaging information 17 indicates each imaging condition (for example, an imaging position, an imaging posture of a provider of mandible model, an angle for taking an image, a rotation, a type of imaging apparatus, values of tube current and tube voltage, a density profile of image, and an image contrast). Meanwhile, the provider information 18 indicates, for example, the age, the gender, the history of past disease (for example, a periodontal disease and maxillary sinusitis), healing history, and medical history of the provider of mandible model; and morphometry values of the shape of mandible measured from the obtained panoramic image 4 (thickness of a cortical bone and a density value). The restoration data 34 where the contour shape is restored can be created from the obtained contour model data 15. The constructed contour model database 19 is stored in a storage unit 38 (corresponding to a hard disk drive) inside of the computer main body 10. The stored contour model database 19 can be, for example, searched, played, and displayed as necessary through operation of the input unit 12. Then, the construction process of the contour model database 19 is completed.

Next, the diagnosis support computer 3 receives an input of the diagnosis image data 6 (Step S5, see FIG. 6(a)). The diagnosis image data 6 is of the panoramic image 4 taken by the imaging apparatus 8. The panoramic image 4 is a panoramic image of a mandible region of a support-subject examinee who provides the diagnosis support information 7. Subsequently, the edge 31 is extracted from the obtained diagnosis image data 6 (Step S6, see FIG. 6(b)). This extraction is performed with the image analysis technique using the Canny filter. A mask process is preliminary performed using a mask pattern (Step S7, see FIG. 6(c)). That is, the mask process is performed to extract only the peripheral of the mandible region and to eliminate edge portions other than the peripheral, thus creating the edge data 22 (Step S8, see FIG. 6(d)). The obtained edge data 22 includes the contour of mandible. The edge 31 may be detected using only the image analysis technique. Alternatively, in the case where the remaining unnecessary edges 31 can be visually checked, a step of manually removing the unnecessary edge portions may be added as necessary.

Next, a process of searching the similar contour model data 15 is performed. That is, the obtained edge data 22 is collated with the plurality of contour model data 15 stored in the contour model database 19, and the most similar contour model data 15 is searched. The similarity search process can be performed on all the contour model data 15 stored in the contour model database 19. Alternatively, the similarity search process may be performed with limiting data to be searched by setting various search conditions (for example, a gender or an age). Here, information on data to be searched is included in the imaging information 17 and the provider information 18 stored together with the contour model data 15.

Figure 7:
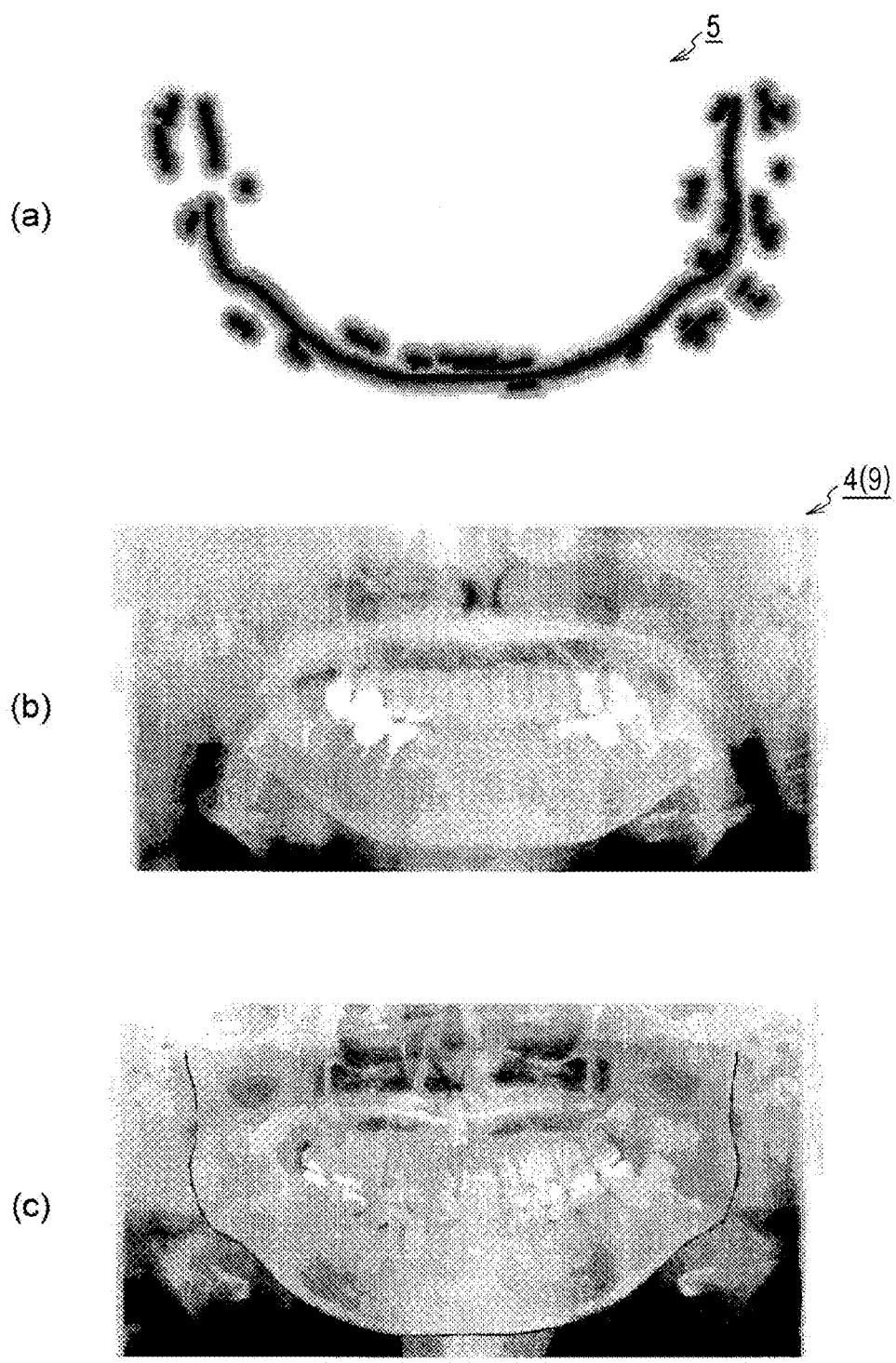
FIG. 7(a) is an explanatory view illustrating a range image.
FIG. 7(b) is a panoramic radiograph found by the similarity search.
FIG. 7(c) is an explanatory view illustrating an exemplary detected contour shape of mandible using an active contour model.
Figure 8:
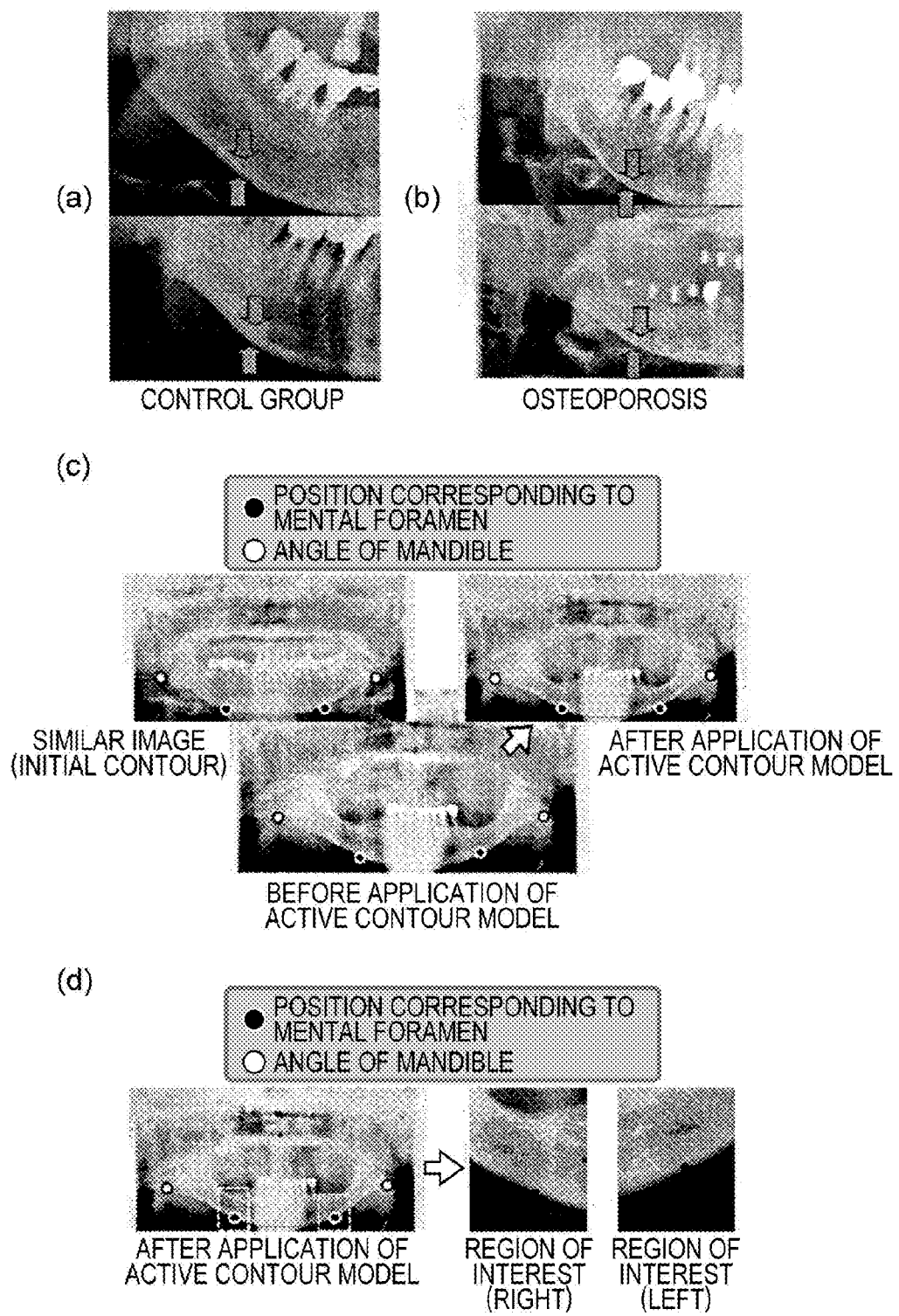
FIG. 8(a) is an explanatory view illustrating an exemplary cortical bone of an able-bodied person.
FIG. 8(b) is an explanatory view illustrating an exemplary a cortical bone of a patient with osteoporosis.
FIG. 8(c) is an explanatory view illustrating determination of positions corresponding to mental foramens and angles of mandible using an active contour model.
FIG. 8(d) is an explanatory view illustrating an exemplary region of interest setting for measuring a thickness of mandibular cortical bone.

Next, a specific method for searching the similar contour model data 15 will be described. First, the range image 5 is created from the edge data 22 (Step S9, see FIG. 7(a)). This edge data 22 is obtained using a Euclidean distance transformation process technique, which is well-known in the image analysis technique. Here, as shown in FIG. 7(a), the lower the pixel value of the created range image 5 (that is, the more the created range image 5 is close to black), the smaller a distance from the edge 31 of mandible is. This allows specifying the contour shape of mandible based on the edge data 22. Meanwhile, the above-described contour shape is restored based on each contour model data 15 stored in the contour model database 19 (Step S10). The restored restoration data 34 is superimposed with the created range image 5, thus calculating an average value on the contour (Step S11). That is, how extent the contour position of the restoration data 34 is shifted from the contour position of the range image 5 is calculated, and the average value is obtained. As a result, the contour model data 15 where the calculated average value of the contour shape of mandible is the minimum is specified (Step S12). Thus, the contour model data 15 similar to the diagnosis image data 6 is determined (see FIG. 7(*b*)).

Next, based on the imaging information 17 of the contour model data 15 determined by the process, whether radiographic imaging conditions of the diagnosis image data 6 (for example, an imaging position) are appropriate or not is judged (Step S13). That is, the imaging information 17 storing various imaging conditions or similar condition is preliminarily associated to the specified contour model data 15. In other words, the imaging information 17 includes information on whether the contour model data 15 has been taken under the appropriate imaging conditions or not. Here, when the imaging position, the imaging posture, and similar condition of the contour model data 15 are the appropriate imaging conditions (YES in Step S13), that is, when the contour model data 15 found by the similarity search based on the imaging information 17 has been taken under the appropriate imaging conditions, the image quality of the contour model data 15 is judged (Step S14). Meanwhile, when the imaging position or similar condition is an inappropriate condition (NO in Step S13), that is, when the contour model data 15 found by the similarity search based on the imaging information 17 has been taken under an inappropriate imaging condition, termination of providing the diagnosis support information 7 is output to the display unit 11 (Step S15). Then, subsequent processes are terminated (Step S16). That is, when the contour model data 15 found by the similarity search has been taken under the appropriate imaging conditions, the diagnosis image data 6 is also judged as being taken under the appropriate imaging conditions. Meanwhile, when the contour model data 15 has been taken under an inappropriate imaging condition, the diagnosis image data is also regarded as being taken under the inappropriate imaging condition. Accordingly, the contour model database 19 preliminary stores data obtained by taking the panoramic images 4 under a plurality of appropriate imaging conditions and inappropriate imaging conditions for use as criteria for judgment.

Furthermore, whether the image quality is appropriate or not is judged (Step S14). That is, whether the image quality (for example, a density profile and contrast) of the contour model data 15 found by the similarity search is in an appropriate range or not is judged. When the image quality of the contour model data 15 is appropriate (YES in Step S14), the process proceeds to Step S17. Meanwhile, if the image quality of the contour model data 15 is inappropriate (that is, the contour model data 15 found by the similarity search based on the imaging information 17 has been taken under inappropriate imaging conditions with error in, for example, the density profile, NO in Step S14), the process proceeds to a step similar to Step S15 and Step S16. That is, termination of providing the diagnosis support information 7 is output (Step S18), and subsequent processes are terminated (Step S19). Accordingly, the subsequent processes are performed only on the diagnosis image data 6 of the panoramic image 4 taken under the appropriate imaging conditions. That is, in the case where diagnosis is performed based on the panoramic image 4 taken under inappropriate imaging conditions, the panoramic image 4 is probably blurred or out of focus. This likely causes questioning judgment of a disease. Therefore, only the panoramic image 4 taken under the appropriate imaging conditions is used for diagnosis. Use of such panoramic image 4 for diagnosis enhances accuracy of the diagnosis support information 7 according to the diagnosis support system 1 of this embodiment.

Then, a disease with a high risk of contraction for the examinee is inferred based on the contour model data 15 judged as appropriate both in, for example, the imaging position and the image quality (Step S17). Here, the provider information 18 is stored being associated with each contour model data 15. The provider information 18 includes basic information, such as the gender of the provider of mandible model, and medical information, such as healing history and disease history of the provider of mandible model. Information on the contracted disease and past diseases of the provider of mandible model is extracted from the provider information 18, and the extracted information is output as the diagnosis support information 7 (Step S20). That is, the morbidity risk of the examinee who provided the diagnosis image data 6 can be predicted based on the provider information 18 of the provider of mandible model whose contour shape of mandible is similar to that of the examinee. A doctor or similar person finely interprets the panoramic image 4 of the examinee based on the provided diagnosis support information 7. This allows judging possibility of acquiring the disease. That is, information on, for example, a disease to be preliminarily noted can be provided to a doctor in interpretation, and the doctor can promptly judge diagnosis of the disease. This allows preventing a judgment error or similar error in advance.

Next, a process to detect a systemic disease based on the diagnosis image data 6 for which the judgment of the appropriate imaging conditions and the provision of the diagnosis support information 7 have been made will be described. First, the contour of mandible is extracted from the diagnosis image data 6 whose diagnosis support information 7 has been provided (Step S21). Specifically, the process is performed using the contour model data 15 already found by the similarity search in the previous step (see FIG. 7(*c*)). At this time, the contour of mandible of the contour model data is set as an initial contour shape. Next, the contour is detected applying an active contour model such that the active contour model may be converged to the edge 31 of the already created edge data 22. Here, description of image analysis applying the active contour model will not be further elaborated here. Then, the process of providing a doctor or similar person with the diagnosis support information 7 is completed (Step S22).

The diagnosis support computer 3 of the diagnosis support system 1 according to the first embodiment may further include a disease detection unit (not shown). This disease detection unit provides information on the region of interest of systemic disease from the contour shape of mandible based on the diagnosis image data 6 where appropriate imaging conditions have been judged and the diagnosis support information 7 on a disease has been provided by the above-described processes. Specifically, the disease detection unit allows detection of osteoporosis, detection of calcification in carotid artery, and detection of maxillary sinusitis. Therefore, this allows automating determination of the region of interest in development of a computer algorithm to judge the disease from the panoramic image 4. This substantially reduces a workload of a doctor or similar person. The following describes an exemplary disease detection unit.

Knowledge up to the present has revealed the following. That is, in the case where the panoramic image 4 of mandible region of osteoporosis patient is taken, the panoramic image of the cortical bone of osteoporosis patient (see FIG. 8(*b*)) is drawn thinner than that of an able-bodied person (control group, see FIG. 8(*a*)). In this case, to obtain good detection property of osteoporosis, measuring thickness of mandibular cortical bone at a position corresponding to a portion referred to as a mental foramen is known (see Non-Patent Document 10). Accordingly, when the mandible model data 9 of the provider of mandible model is stored in the contour model database 19, a coordinate corresponding to the mental foramen is preliminarily recorded. Subsequently, when the initial contour shape is obtained in the above-described process, the coordinate is arranged. Then, a coordinate after application of the active contour model is determined as a region of interest (namely, a position corresponding to the mental foramen) (FIG. 8(*c*)). Consequently, a peripheral position of the mental foramen can be set as the region of interest for measuring the thickness of the mandibular cortical bone (FIG. 8(*d*)).

Meanwhile, carotid arteries are disposed at a lower side and outward of the angle of mandible in the panoramic image 4. Calcification in carotid artery is drawn as a region in which the density has a locally high value (see the arrows in FIG. 9(*a*)). Accordingly, the position of the angle of mandible can be automatically determined and based on the determination, a region of interest to detect the calcification in carotid artery can be automatically set (see Non-Patent Document 11). Since the angle of mandible can be determined by a method similar to determination on a position corresponding to the above-described mental foramen of osteoporosis, the description will not be further elaborated here. This allows setting only regions of lower side and outward of the angle of mandible as the region of interest to detect the calcification in carotid artery (see FIG. 9(*b*)).

As described above, the diagnosis support system 1 according to the first embodiment uses the panoramic image 4 where the mandible region of examinee is taken, performs similarity search on the preliminarily constructed contour model database 19, and finds the corresponding contour model data 15. Based on the imaging information 17 and the provider information 18 associated with the contour model data 15, degree of appropriateness of the imaging conditions and the diagnosis support information 7 on a disease that the examinee is likely to be affected can be provided. That is, judging appropriateness based on the imaging information 17 allows eliminating diagnosis based on the panoramic image 4 taken under inappropriate imaging conditions. Consequently, accuracy of diagnosis is enhanced. Further, based on similarity in the contour shape of mandible, a disease with a high risk of contraction can be preliminary suggested to the examinee. The disease with a high risk of contraction can be preliminary provided as beneficial information to, for example, a doctor who actually diagnoses the examinee. This allows the doctor to diagnose a disease suggested in diagnosis correctly. As a result, a mistake of overlooking the disease in interpretation of the panoramic image can be prevented in advance.

Figure 11:
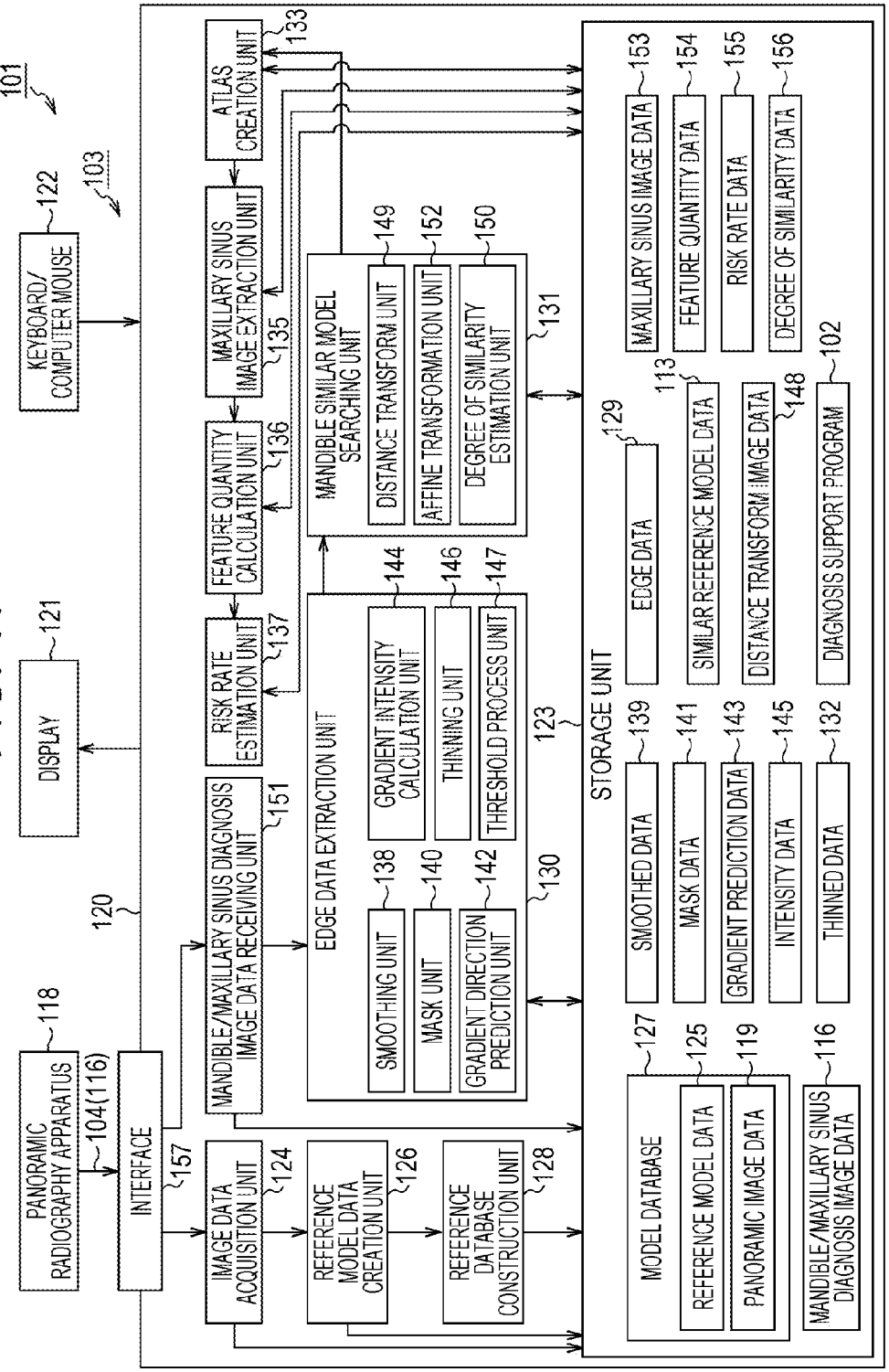
FIG. 11 is a block diagram illustrating a functional configuration of a diagnosis support computer in a diagnosis support system according to a second embodiment.

A description will be given of a diagnosis support system 101 and a diagnosis support program 102 according to the second embodiment of the present invention with reference to FIG. 11 to FIG. 19. The diagnosis support system 101 and the diagnosis support program 102 judge degree of appropriateness of imaging conditions according to the first embodiment, and then provide information on diagnosis of odontogenic maxillary sinusitis. The diagnosis support system 101 according to the second embodiment, as shown in FIG. 11 and similar drawing, receives an input of mandible/maxillary sinus diagnosis image data 116 of a test object image 104 (the panoramic image) where a region including a mandible and maxillary sinuses of the examinee has been taken. Then, the diagnosis support system 101 performs various image analyses on the mandible/maxillary sinus diagnosis image data 116 and extracts maxillary sinus image data 153 from the mandible/maxillary sinus diagnosis image data 116. Accordingly, the diagnosis support system 101 provides information beneficial for diagnosing an odontogenic maxillary sinusitis based on the maxillary sinus image data 153. The diagnosis support system 101 is mainly constituted of a diagnosis support computer 103.

Here, panoramic image data and the test object image 104 are obtained using a panoramic radiography apparatus 118 (hereinafter simply referred to as a imaging apparatus 118). Subjects to be imaged of, for example, a model data provider (not shown) and a head phantom for radiographic imaging; and a subject to be imaged including regions of the mandible and maxillary sinuses of each examinee to be diagnosed are taken as the panoramic image data and the test object image 104. The imaging apparatus 118 is directly coupled to the diagnosis support computer 103. The imaging apparatus 118 can electrically take the test object image 104 as the panoramic image data 119 or the mandible/maxillary sinus diagnosis image data 116 directly. The imaging apparatus 118 may not be coupled to the diagnosis support computer 103. In this case, the data may be incorporated and input to the diagnosis support computer 103 through a storage medium such as a CD-ROM and DVD-ROM or a telecommunications line such as the Internet.

The diagnosis support computer 103 used in the diagnosis support system 101 may include a hardware configuration similar to the diagnosis support computer 3 according to the first embodiment. The diagnosis support computer 103 includes a computer main body 120 housed in a casing, a display 121, and a keyboard/computer mouse 122. The diagnosis support computer 103 is electrically coupled to the above-described imaging apparatus 118 via an interface 157. Therefore, the diagnosis support computer 103 can receive, for example, the mandible/maxillary sinus diagnosis image data 116. The computer main body 120 internally includes various hardware. The hardware includes, for example, a Central Processing Unit (CPU), which performs various signal processes, a memory for storing temporary data, and a hard disk drive as a storage unit 123 for storing and memorizing, for example, various information and data (some parts are not shown). The storage unit 123 further stores a diagnosis support program 102. The diagnosis support program 102 allows the diagnosis support computer 103 to function such that the diagnosis support computer 103 may achieve various operational effects of the diagnosis support system 101 according to the present invention. That is, the diagnosis support program 102 has been installed to be operable.

The diagnosis support computer 103, as shown in FIG. 11 and similar drawing, mainly includes an image data acquisition unit 124, a reference model data creation unit 126, a reference database construction unit 128, a mandible/maxillary sinus diagnosis image data receiving unit 151, an edge data extraction unit 130, a mandible similar model searching unit 131, an atlas creation unit 133, a maxillary sinus image extraction unit 135, a feature quantity calculation unit 136, and a risk rate estimation unit 137 as its functional component elements. The image data acquisition unit 124 obtains the panoramic image data 119 of a plurality of panoramic images taken by the imaging apparatus 118. The reference model data creation unit 126 specifies the contour of mandible and regions of maxillary sinuses from the panoramic image data 119 and creates the reference model data 125. The reference database construction unit 128 accumulates and stores the plurality of created reference model data 125 and constructs a model database 127. The mandible/maxillary sinus diagnosis image data receiving unit 151 takes the test object image 104 including regions of mandible and maxillary sinuses of the examinee to be diagnosed and receives an input of the obtained mandible/maxillary sinus diagnosis image data 116. The edge data extraction unit 130 extracts edge data 129 of mandible from the received mandible/maxillary sinus diagnosis image data 116. The mandible similar model searching unit 131 collates the extracted edge data 129 and the reference model data 125 included in the model database 127. The mandible similar model searching unit 131 searches the reference model data 125 with a contour shape of mandible similar to that of the edge data 129. The atlas creation unit 133 specifies regions of maxillary sinuses from the similar reference model data 113 found by the similarity search and creates an atlas 114 of maxillary sinuses. The maxillary sinus image extraction unit 135 extracts the maxillary sinus image 134 corresponding to a region of interest 115 of a right and left pair of maxillary sinuses from the mandible/maxillary sinus diagnosis image data 116 based on the created atlas 114. The feature quantity calculation unit 136 calculates feature quantities from the extracted maxillary sinus image 134. The risk rate estimation unit 137 estimates a risk rate of odontogenic maxillary sinusitis of the mandible/maxillary sinus diagnosis image data 116 from the calculated feature quantities.

Furthermore, the edge data extraction unit 130 includes a smoothing unit 138, a mask unit 140, a gradient direction prediction unit 142, a gradient intensity calculation unit 144, a thinning unit 146, and a threshold process unit 147. The smoothing unit 138 performs a smoothing process to remove noise included in the mandible/maxillary sinus diagnosis image data 116. The mask unit 140 performs a mask process on obtained smoothed data 139 in a range where presence of the mandible is preliminary expected to obtain mask data 141. The gradient direction prediction unit 142 predicts a gradient direction of an edge constituting the contour of mandible in the mask data 141. The gradient intensity calculation unit 144 calculates the gradient and intensity of the edge using a Kirsch method based on the obtained gradient prediction data 143. The thinning unit 146 thins the edge of calculated intensity data 145 by non-maximum suppression process. The threshold process unit 147 performs a hysteresis threshold process on the thinned data 132 obtained by the thinning unit 146 and extracts the edge data 129.

The mandible similar model searching unit 131 further includes a distance transform unit 149, an affine transformation unit 152, and a similarity degree estimation unit 150. The distance transform unit 149 creates distance transform image data 148 based on the edge data 129 extracted from the mandible/maxillary sinus diagnosis image data 116. The affine transformation unit 152 performs an affine transformation on the reference model data 125 stored in the model database 127. The similarity degree estimation unit 150 estimates a degree of similarity between the reference model data 125 where affine transformation has been performed and the edge data 129 and extracts similar reference model data 113.

Since the diagnosis support computer 103 includes the above-described functional component elements, information on possibility of morbidity of odontogenic maxillary sinusitis can be provided from the mandible/maxillary sinus diagnosis image data 116 of the examinee to a dentist or similar person. That is, feature quantities of regions of maxillary sinuses included in the test object image 104 is compared, and a risk rate can be quantitatively suggested corresponding to a magnitude of difference of the feature quantities.

Figure 12:
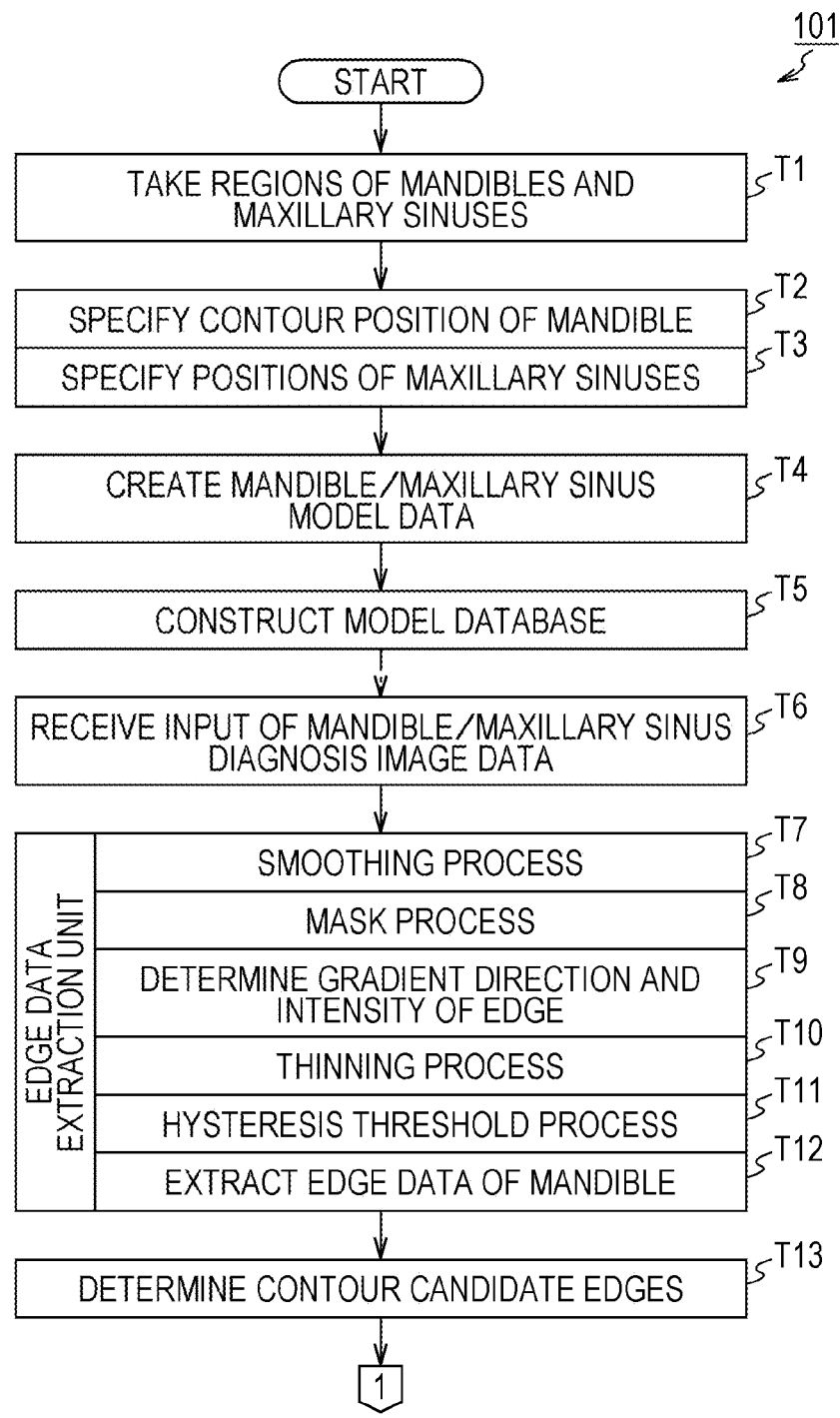
FIG. 12 is a flowchart illustrating a flow of processes by the diagnosis support computer according to the second embodiment.
Figure 13:
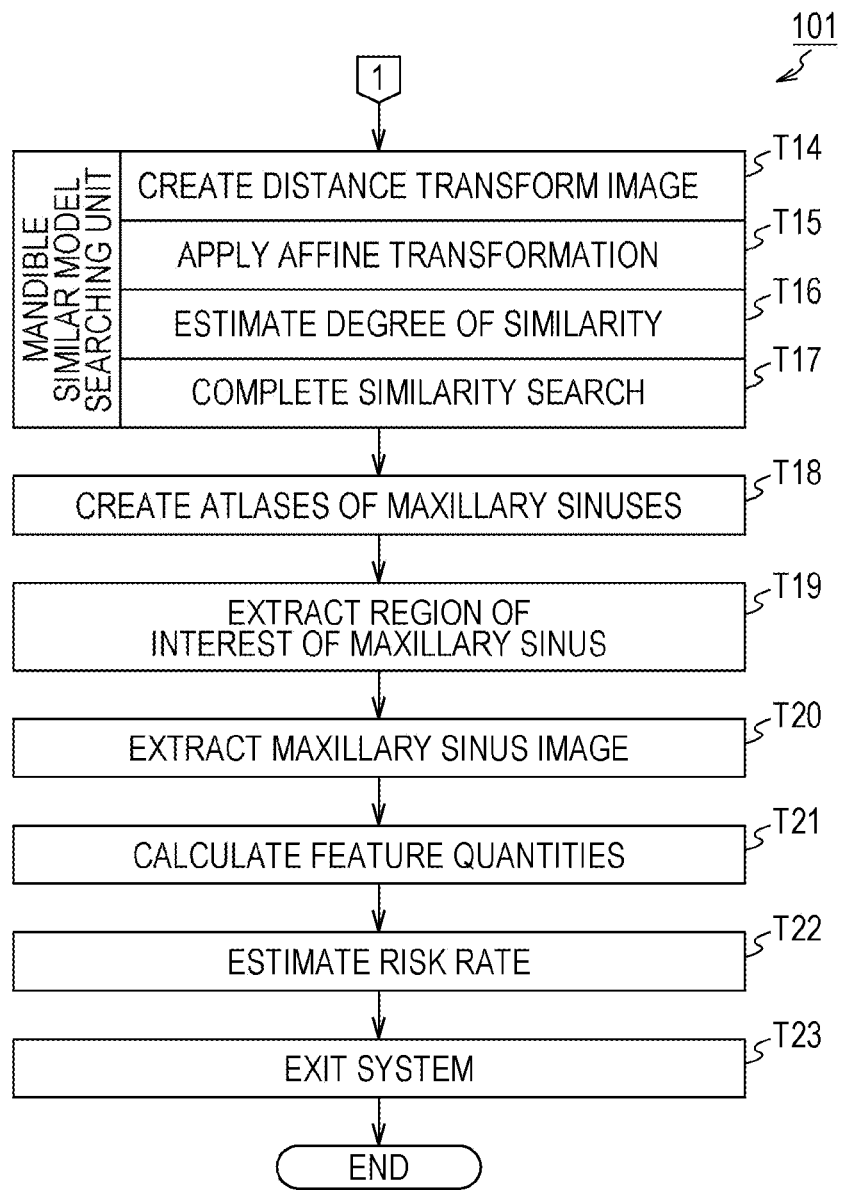
FIG. 13 is a flowchart illustrating a flow of the processes by the diagnosis support computer according to the second embodiment.

A concrete example of a process that the diagnosis support system 101 according to this embodiment provides information on odontogenic maxillary sinusitis will be mainly described with reference to the flowcharts in FIG. 12 and FIG. 13. First, a process of constructing the model database 127 will be described. The model database 127 is searched for the similar reference model data 113 similar to the mandible/maxillary sinus diagnosis image data 116. First, panoramic images where regions of mandibles and maxillary sinuses of a plurality of model data providers are subjects to be imaged are taken using the imaging apparatus 118 (Step T1, see FIG. 14(a)). Here, apart from the living model data provider, the imaging subject may include a head phantom made by artificial bones for radiographic imaging. Thus, the plurality of panoramic image data 119 with different age, gender, and similar condition from one another are obtained. FIG. 14(b) is a schematic view illustrating a structure of human body including general regions of mandible and maxillary sinuses. As apparent from FIG. 14(a) and FIG. 14(b), the contour shape of mandible (namely, the lower edge portion and right and left rear edge portions of mandible) is less affected by presence/absence of tooth, opening/closing state of mouth, or ghost reflections from obstructive shadows, thus making drawing of the panoramic image always stable. Accordingly, the diagnosis support system 101 according to this embodiment uses the contour of mandible as a reference point (a reference region) for specifying a maxillary sinus region.

A taken panoramic image is electrically stored in the storage unit 123 of the diagnosis support computer 103 as the panoramic image data 119. Then, the panoramic image data 119 is processed using a digital filter. As a result, the reference model data 125 where a contour position of the mandible and positions of the maxillary sinus regions are specified is created (Step T2 and Step T3). To describe specifically, an image analysis technique using a Canny filter (Canny method), which is one kind of digital filter, is applied. That is, use of the technique specifies a portion of discontinuous pixel values constituting the panoramic image data 119, and detects the discontinuous portion as a contour portion (Step T2). Further, formulating (modeling) the detected contour portion specifies the contour shape of mandible. Positions of maxillary sinuses to be analyzed (the regions of interest 115) are specified on the same screen (the panoramic image data 119) (Step T3). Here, the region of interest 115 may be specified by, for example, manually pointing a point or a region in the panoramic image data 119 (the test object image 104) displayed on the screen by, for example, a dentist.

At this time, the region of interest 115 may be specified along an outline of the maxillary sinus. Alternatively, the region of interest 115 may be specified by simple drawing such as a rectangular. The reference model data 125 including specific information on the specification of a contour shape and the region of interest 115 of maxillary sinus is created (Step T4). The process is repeated on the plurality of panoramic image data 119. Thus, each reference model data 125 is created from the individual panoramic image data 119, which is input to the diagnosis support computer 103, and then is accumulated. Here, each reference model data 125 includes information on positions of right and left pair of maxillary sinuses as well as information on the contour shape of mandible. The reference model data 125 also includes information where a positional relationship of the maxillary sinuses relative to the mandible is described. Accordingly, the position of mandible is specified using the reference model data 125. Consequently, the position of maxillary sinuses corresponding to the position of mandible can be inevitably determined. Accumulation of the plurality of reference model data 125 constructs the model database 127 (Step T5).

The panoramic image data 119 obtained by the imaging apparatus 118 includes information on each imaging condition and similar information, information on an age, gender, past disease history, and similar information of the provider of reference model, and information on morphometry of, for example, a mandible measured from the test object image 104 (for example, a thickness of cortical bone). These information may be associated with the created reference model data 125 and stored together in the constructed model database 127 (not shown). The constructed model database 127 is stored in the storage unit 123 of the diagnosis support computer 103. The model database 127 can be read out from the storage unit 123 as necessary according to an operation using an operating unit such as the computer mouse 122. A well-known technique using a P-type Fourier descriptor is applicable to a modeling process of the contour shape of mandible. Details of the modeling process using this technique will not be further elaborated here. Then, the construction of the model database 127 is completed. In FIG. 12 and FIG. 13, the process of constructing the model database 127 and a process on the mandible/maxillary sinus diagnosis image data 116, which will be described below, are consecutively performed. However, this should not be construed in a limiting sense. For example, after performing processes of Step T1 to Step T5 (construction of the model database 127), a process may be started from Step T6 as necessary.

After completion of construction of the model database 127, the diagnosis support computer 103 receives an input of the mandible/maxillary sinus diagnosis image data 116 of the test object image 104 (Step T6, see FIG. 14(*a*)). Here, the test object image 104 includes regions of mandible and maxillary sinuses of the examinee to be diagnosed taken by the imaging apparatus 118. Then, an image analysis process using a digital filter is performed on the received mandible/maxillary sinus diagnosis image data 116. This process extracts the edge data 129 of the contour of mandible (the edge) (Step T7 to Step T13: equivalent to the edge data extraction unit 130). Here, for extraction of the edge data 129, the diagnosis support system 101 according to this embodiment applies the Kirsch method as well as a process using the Canny filter. This allows extracting further minute edge data 129 from the mandible/maxillary sinus diagnosis image data 116 based on information on a gradient direction and intensity of the edge.

To describe specifically, the mandible/maxillary sinus diagnosis image data 116 input from the imaging apparatus 118 is received via the interface 157. Then, a smoothing process using a Gaussian filter is performed on the mandible/maxillary sinus diagnosis image data 116 to remove noise included in the mandible/maxillary sinus diagnosis image data 116 (Step T7, see FIG. 14(*c*)). This converts the mandible/maxillary sinus diagnosis image data 116 into the smoothed data 139. At this time, defining a pixel value at row i and column j in two-dimensional digital image as f (i, j), the Gaussian filter is represented by the following expression 1.

$$f(i, j) = \frac{1}{2\pi\sigma^2}\left(-\frac{i^2 + j^2}{2\sigma^2}\right) \quad \text{(Expression 1)}$$

Here, σ indicates a standard deviation. At this time, a small σ value reduces smoothing effect. Meanwhile, the smoothing effect increases with increasing σ value. A position where the mandible is expected to be present in the obtained smoothed data 139 is defined as a mask region. A template where a specific edge pattern is assumed is prepared for each mask region, and matching is performed by Kirsch method (Step T8, see FIG. 15(*a*)). Here, the mask region R∈M where a mask image 107 in FIG. 15(*a*) is M and M={m (i, j)} is divided into seven subregions ($R_1, R_2, \ldots R_7$). The Rs ($R_1, R_2, \ldots R_7$) will be described individually. Considering the shape of mandible (see, for example, FIG. 14(*a*)), the edge of the contour of mandible is predictable. That is, $R_1$ and $R_7$ at both end sides edges are predictable as edges in the longitudinal direction while $R_4$ at the center is predictable as an edge in the lateral direction. Based on the preliminary available knowledge, the gradient direction and the intensity of the edge are determined based on the following expression (Expression 2) by Kirsch method (Step T9).

$$f_2(i, j) = \begin{cases} \sum_{x=-1}^{1}\sum_{y=-1}^{1} g_{xy}^{(1)} \cdot f(i+x, j+y) & \text{if } f(i, j) \in R_1 \\ \max_{z=1,2}\sum_{x=-1}^{1}\sum_{y=-1}^{1} g_{xy}^{(z)} \cdot f(i+x, j+y) & \text{if } f(i, j) \in R_2 \\ \sum_{x=-1}^{1}\sum_{y=-1}^{1} g_{xy}^{(2)} \cdot f(i+x, j+y) & \text{if } f(i, j) \in R_3 \\ \sum_{x=-1}^{1}\sum_{y=-1}^{1} g_{xy}^{(3)} \cdot f(i+x, j+y) & \text{if } f(i, j) \in R_4 \\ \sum_{x=-1}^{1}\sum_{y=-1}^{1} g_{xy}^{(4)} \cdot f(i+x, j+y) & \text{if } f(i, j) \in R_5 \\ \max_{z=4,5}\sum_{x=-1}^{1}\sum_{y=-1}^{1} g_{xy}^{(z)} \cdot f(i+x, j+y) & \text{if } f(i, j) \in R_6 \\ \sum_{x=-1}^{1}\sum_{y=-1}^{1} g_{xy}^{(5)} \cdot f(i+x, j+y) & \text{if } f(i, j) \in R_7 \\ 0 & \text{otherwise} \end{cases} \quad \text{(Expression 2)}$$

where the direction kernels $$g^{(1)} = \begin{bmatrix} -3 & -3 & +5 \\ -3 & 0 & +5 \\ -3 & -3 & +5 \end{bmatrix},$$

$$g^{(2)} = \begin{bmatrix} -3 & +5 & +5 \\ -3 & 0 & +5 \\ -3 & -3 & -3 \end{bmatrix},$$

$$g^{(3)} = \begin{bmatrix} +5 & +5 & +5 \\ -3 & 0 & -3 \\ -3 & -3 & -3 \end{bmatrix},$$

$$g^{(4)} = \begin{bmatrix} +5 & +5 & -3 \\ +5 & 0 & -3 \\ -3 & -3 & -3 \end{bmatrix},$$

$$g^{(5)} = \begin{bmatrix} +5 & -3 & -3 \\ +5 & 0 & -3 \\ +5 & -3 & -3 \end{bmatrix},$$

Figure 15:
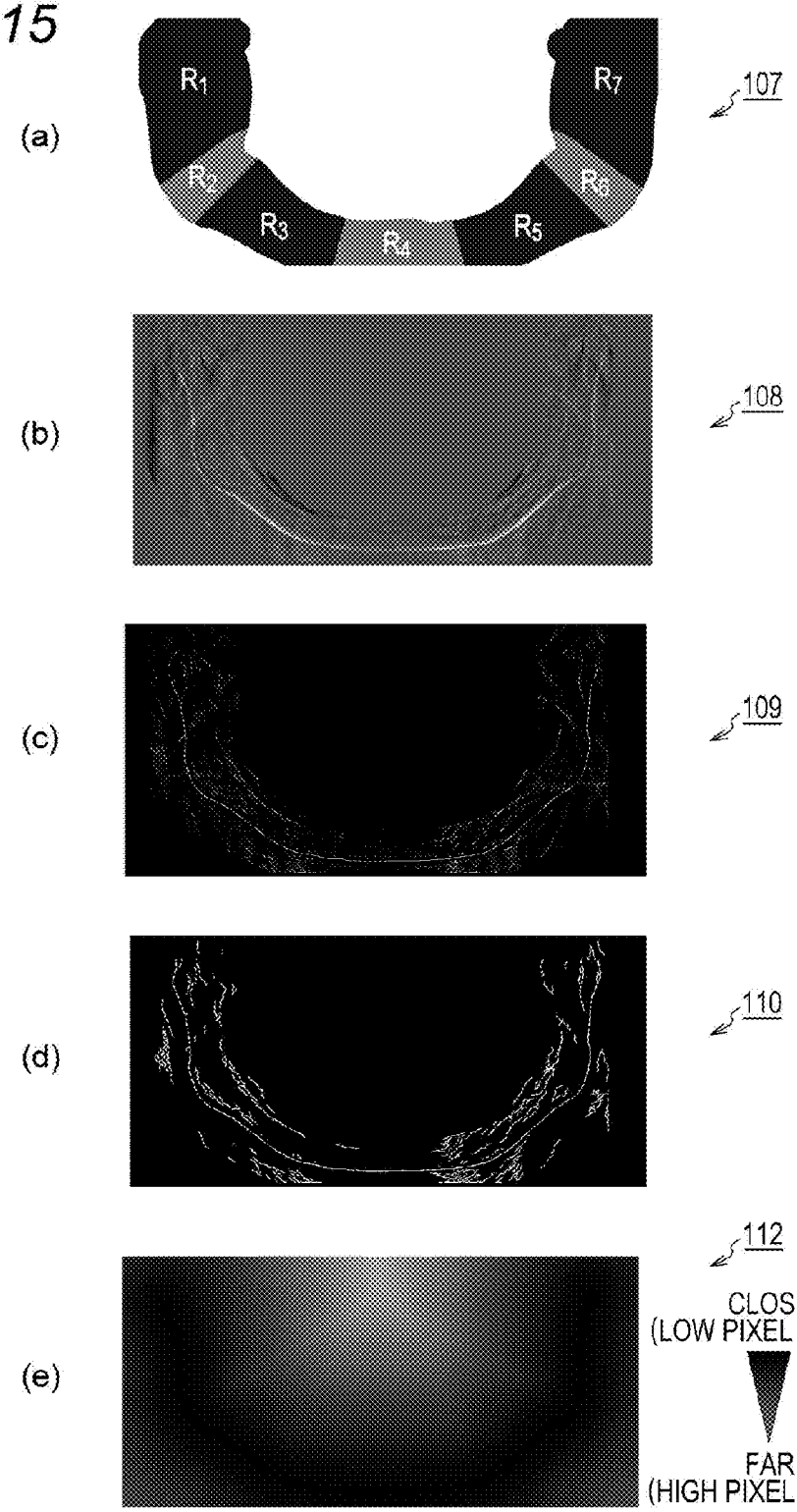
FIG. 15(a) is an explanatory view illustrating a mask image.
FIG. 15(b) is an explanatory view illustrating an edge-enhanced image.
FIG. 15(c) is an explanatory view illustrating a thinned image.
FIG. 15(d) is an explanatory view illustrating an edge image.
FIG. 15(e) is an explanatory view illustrating a distance transform image.

An exemplary edge-enhanced image 108 where the edge intensity has been calculated based on the expression is shown in FIG. 15(*b*). Here, the edge-enhanced image 108 obtained by Kirsch method is prone to have an individual thick line drawing due to the Gaussian filter at the smoothing process. The thick line drawing is thinned by non-maximum suppression process (Step T10). Here, the non-maximum suppression process compares a value of intensity data 145 of a preliminary calculated edge and pixel values adjacent to the edge in the vertical direction and changes the value to 0 if the value is not the maximum value. A thinned image 109 obtained by this process is shown in FIG. 15(*c*).

Next, the edge is detected from the obtained thinned data 132 by hysteresis threshold process (Step T11). Here, the hysteresis threshold process specifies two thresholds, a low value (a lower limit value) and a high value (an upper limit value), and performs the following judgment. That is, (1) a pixel with intensity value higher than the upper limit value is regarded as an edge, (2) a pixel with intensity value lower than the lower limit value is regarded as non-edge, (3) among pixels with intensity value equal to or more than the lower limit value and equal to or less than the upper limit value, a pixel united with the edge is regarded as an edge.

Then, all edges obtained by the process are labeled to extract the edge of the contour of mandible (Step T12). Here, considering a characteristic of an imaging technique taking the test object image 104, both right and left ends and the center of the test object image 104 and a periphery of the angle of mandible are affected by obstructive shadow of cervical vertebra and the angle of mandible on the opposite side. Meanwhile, the proximity of the mental foramen is stably drawn comparatively. Therefore, the rear edge portion of a ramus of mandible is also stably drawn insofar as the patient is positioned appropriately and the shadow of the cervical vertebra is not superimposed. Application of the hysteresis threshold process is prone to detect the edge of the contour of mandible as an edge longer than other edges.

The longest edge in the lateral direction near the mental foramens ($R_3$ and $R_5$ in FIG. 15(*a*)) and the longest edge in the longitudinal direction at the rear edge portions of ramus of mandible ($R_1$ and $R_7$ in FIG. 15(*a*)) are determined as the contour of angle of mandible. Then, edges adjacent to the edges determined as the contour of mandible in regions other than the regions ($R_2$, $R_4$, and $R_6$ in FIG. 15(*a*)) are also determined as the contour of mandible. Thus, contour candidate edges of the mandible are determined (Step T13). Accordingly, using the Canny filter and the Kirsch method, the edge data 129 of the shape (the edges) of the contour of mandible is specified from the mandible/maxillary sinus diagnosis image data 116.

Next, based on the contour of mandible (the edge data 129) obtained from the process, the constructed model database 127 is searched for the similar reference model data 113 (Step T14 to Step T17). To describe specifically, an image of F={$f_3$ (i, j)} where the pixel value of the candidate edge of the contour of mandible of the mandible/maxillary sinus diagnosis image data 116 is 0 and the pixel values other than that is 1 is searched. D={d(i, j)} is defined as a distance transform image 112. At this time, the D is determined by the following expression (Expression 3).

$$D = \{d(i,\ j)\} = \min_{(p,q)} \left\{ \sqrt{(i-p)^2 + (j-q)^2} \right\} \Big|\ f_3(p,\ q) = 0, \quad \text{(Expression 3)}$$

Here, the distance transform image 112 where distance transform is applied (distance transform image data 148) is shown in FIG. 15 (Step T14). Accordingly, the lower the pixel value (closer to black), the more approximate to the edge data 129 of the contour of the mandible is. Meanwhile, the higher the pixel value (white), the farther from the edge data 129 at the contour of the mandible is. Therefore, defining the k-th reference model data 125 as $M_k$={m (i, j)}, and affine transformation is applied (Step T15). Here, assuming the reference model data 125 after applying affine transformation as M'k={m' (i, j')}, the reference model data 125 can be represented by the following expression (Expression 4).

$$m'(i',\ j') = \begin{pmatrix} a & b \\ c & d \end{pmatrix} \begin{pmatrix} i \\ j \end{pmatrix} + \begin{pmatrix} e \\ f \end{pmatrix}, \quad \text{(Expression 4)}$$

Here, a, b, c, d, e, and f are any given coefficient values in affine transformation. The coefficient values are set such that an output value of the expression shown below (Expression 5) may be low. Then, a degree of similarity (degree of similarity data 156) between the reference model data 125 and the mandible/maxillary sinus diagnosis image data 116 are estimated (Step T16).

$$Sim(M'_k,\ F) = \quad \text{(Expression 5)}$$
$$\operatorname*{mean}_{(p,q)} \{d(p,\ q)\ |\ m'(p,\ q) = \text{Pixel on contour of mandible}\},$$

Figure 16:
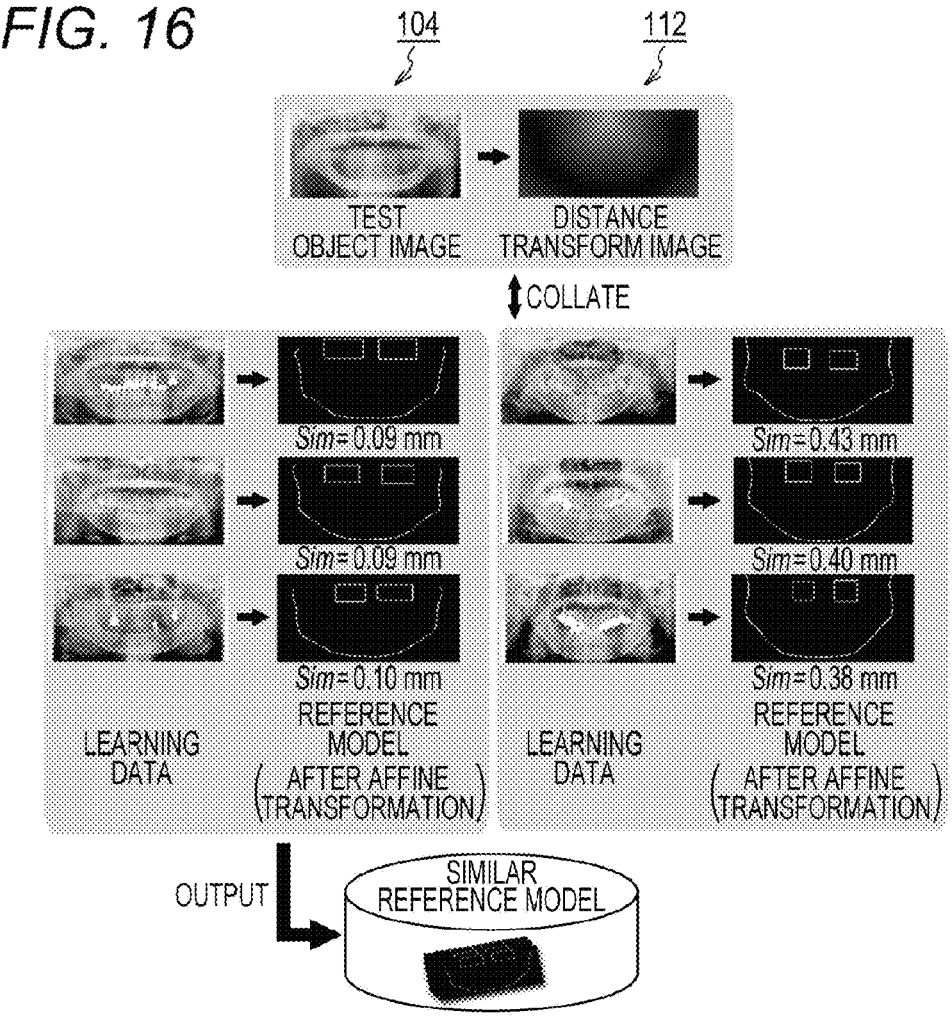
FIG. 16 is an explanatory view illustrating an exemplary distance transform image.

In the formula, a low output value means that the reference model data 125 ($M'_k$) is similar to the mandible/maxillary sinus diagnosis image data 116. This specifies the similar reference model data 113, completing similarity search (Step T17). Here, only the one similar reference model data 113 with the highest degree of similarity (a lowest output value) may be output as the similar reference model data 113 found by the similarity search. Alternatively, a plurality of models may be output in order of higher degree of similarity as the similar reference model data 113 found by the similarity search. Alternatively, all the similar reference model data 113 with less than a preset threshold may be output as the similar reference model data 113 found by the similarity search. FIG. 16 depicts an output result of the similar reference model data 113 whose evaluation value (Sim) obtained by the expression is equal to or less than 0.10 mm.

Afterwards, regions of maxillary sinuses are extracted from the similar reference model data 113 found by the similarity search, and then the atlas 114 of maxillary sinus is created (Step T18). In this example, the diagnosis support system 101 according to this embodiment creates the atlas 114. At that time, the plurality of similar reference model data 113 found by the above similarity search process is used. Here, $n_2$ ($1 \leq n_2 \leq n_1$) indicates the number of similar reference model data 113. $I_k$ (i, j) is a function defined as follows. That is, in the case where the pixel (i, j) of the k-th similar reference model data 113 is in the region of maxillary sinus, $I_k$ (i, j) is a function that returns 1. Meanwhile, in the case where the pixel (i, j) is out of the region of maxillary sinus, $I_k$ (i, j) is a function that returns 0. When $I_k$ (i, j) is defined like this, the atlas 114 of maxillary sinus is determined by the following expression (Expression 6).

$$P_{atlas}(i, j) = \frac{1}{n_2} \sum_{k=1}^{n_2} I_k(i, j), \quad \text{(Expression 6)}$$

At this time, the atlas 114 of maxillary sinus is specified in a range of 0 to 1 corresponding to probability of presence of maxillary sinus. Furthermore, a threshold process specifies the region of interest 115 of maxillary sinus (Step T19). At this time, assuming G={f4(i, j)} is an image where the pixel of the region of interest 115 of maxillary sinus as 1 and the pixel of the regions other than the region of interest 115 of maxillary sinus as 0, G={f4(i, j)} is defined by the following expression (Expression 7).

$$G = \{f_4(i, j)\} = \begin{cases} 1 & \text{if } P_{atlas}(i, j) \geq \alpha, \\ 0 & \text{otherwise} \end{cases} \quad \text{(Expression 7)}$$

Figure 17:
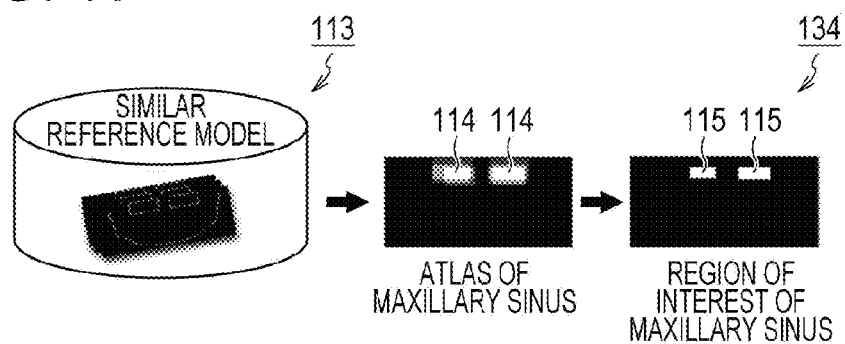
FIG. 17 is an explanatory view illustrating an atlas created from similar reference model data and regions of interest of maxillary sinuses.

Here, α denotes an any given fixed threshold. The atlas 114 of maxillary sinus is created from the above-described similar reference model data 113 in FIG. 16. FIG. 17 depicts an exemplary image where the region of interest 115 of maxillary sinus is specified assuming α=1. Here, in FIG. 17, the atlas 114 is created by superimposing the three similar reference model data 113. Here, the atlases 114 are displayed in white pixels to the extent that the probability they are maxillary sinus regions is high. Only pixels where all the three similar reference model data 113 are superimposed are extracted in the region of interest 115 of the maxillary sinus by threshold process. That is, the diagnosis support system 101 according to this embodiment superimposes the region of interest 115 of maxillary sinus specified by the reference model data 125 over one or the plurality of similar reference model data 113 found by the similarity search. This superimposition creates the atlas 114 corresponding to the contour of mandible (the edge data 129).

Figure 18:
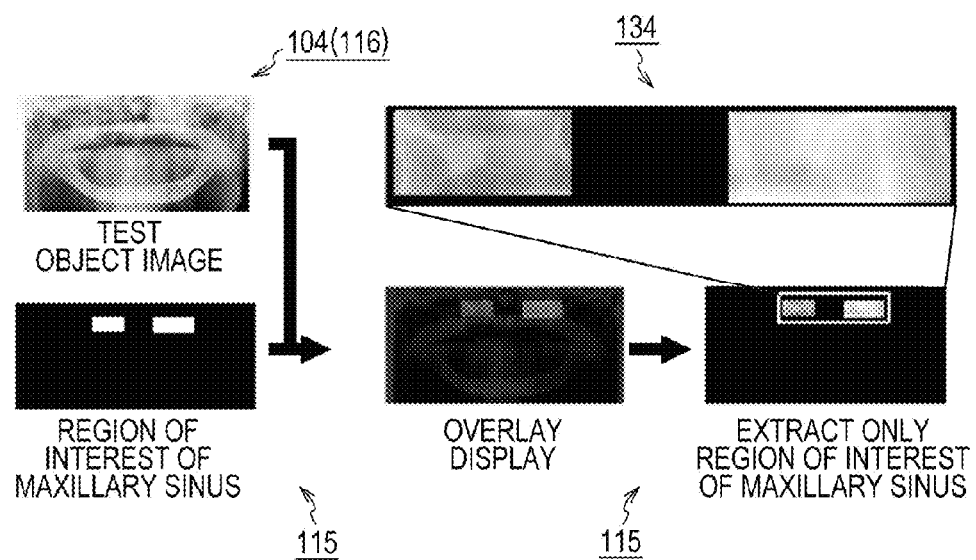
FIG. 18 is an explanatory view illustrating a result where the regions of interest of the maxillary sinuses are extracted from the test object image.
Figure 19:
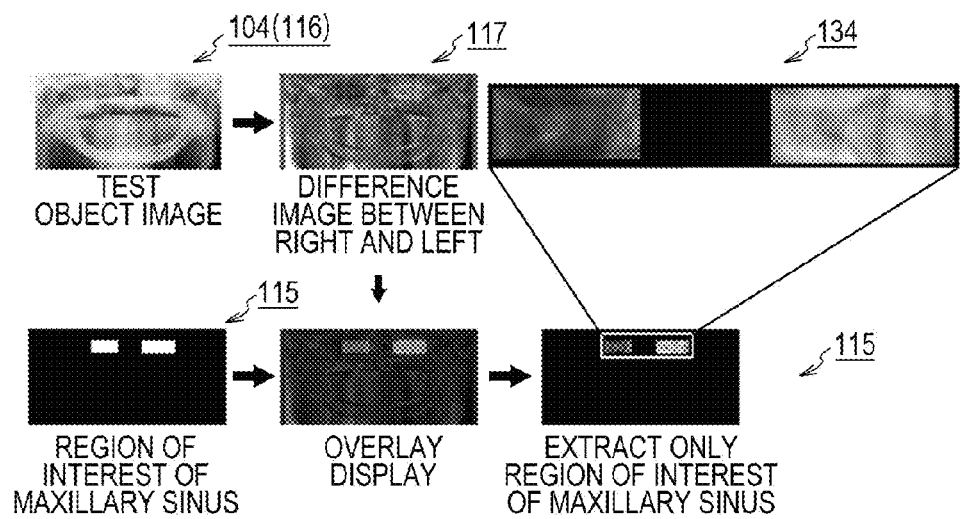
FIG. 19 is an explanatory view illustrating a result where the regions of interest of the maxillary sinuses are extracted from a contralateral subtraction image of the test object image.

Based on the region of interest 115 of maxillary sinus obtained by the process, the maxillary sinus image 134 (maxillary sinus image data 153) is extracted from the mandible/maxillary sinus diagnosis image data 116 (Step T20) (see FIG. 18). This automatically extracts a region corresponding to a maxillary sinus from the mandible/maxillary sinus diagnosis image data 116. Using the edge data 129 for the contour of mandible as standard reference and based on the plurality of similar reference model data 113, the atlas 114 is created and the region of interest 115 is specified. Accordingly, the maxillary sinus image 134 obtained by the extraction process correctly indicates the position of the maxillary sinus of the examinee. As shown in FIG. 19, a contralateral subtraction image 117 of the mandible/maxillary sinus diagnosis image data 116 may be created, and the regions of maxillary sinuses may be extracted from the contralateral subtraction image 117. Next, feature quantities (feature quantity data 154) of the regions of maxillary sinuses (the maxillary sinus image 134) extracted by the process is calculated (Step T21). Here, the feature quantities correspond to, for example, a mean value, a median, a mode, a standard deviation, a histogram distribution of pixels constituting the regions of maxillary sinuses, and the size of the region. The feature quantities are quantitatively indicated to the right and left maxillary sinuses placing the nose as the center, respectively.

Then, based on the calculated feature quantity data 154, difference between regions of right and left maxillary sinuses of the examinee is compared. A risk rate (degree of risk data 155) is estimated based on the comparison result (Step T22). Here, the risk rate may be expressed as follows. That is, for example, a degree of risk rate is preliminarily defined. Based on the definition, the risk rate is expressed in value (for example, 70% or 80%) in accordance *ith the magnitude of difference in the calculated feature quantity data 154. Alternatively, the risk rate may be obtained from a rate of change in the feature quantities of maxillary sinus on the side affected by odontogenic maxillary sinusitis in relation to feature quantities on the normal maxillary sinus side. This quantitatively indicates both the feature quantities and the risk rate. This allows a dentist or similar person to be provided information on possibility of odontogenic maxillary sinusitis from the test object image 104. This also allows the dentist or similar person to make final judgment from interpretation of the panoramic image, re-examination, or similar method. Consequently, the panoramic image, which is taken daily in a dental clinic or similar place, can provide beneficial information. Furthermore, a large amount of panoramic images can be processed like this. Accordingly, even in the case where panoramic images of many examinees are taken (for example, dental checkup), the process is effective for initial judgment on suspicion of odontogenic maxillary sinusitis. Information on the feature quantities and the risk rate are output and displayed on the display 121. Then, the diagnosis support system 101 according to the embodiment completes the process (Step T23).

As described above, the diagnosis support system 101 according to this embodiment can determine the edge data 129 of the mandible from the test object image 104 taken including the mandible and the maxillary sinuses of the examinee. The diagnosis support system 101 searches the panoramic image data 119 and the reference model data 125 in the preliminary constructed model database 127 for the similar reference model data 113 similar to the edge data 129, and then creates the atlases 114 of the maxillary sinuses. The diagnosis support system 101 can specify the regions of interest 115 of maxillary sinuses in the mandible/maxillary sinus diagnosis image data 116, and then extract the maxillary sinus image 134. The diagnosis support system 101 according to this embodiment easily achieves comparison of right and left maxillary sinuses based on feature quantities of the maxillary sinus image 134 by automating these processes. This allows providing suggestion of possibility of odontogenic maxillary sinusitis to a dentist or similar person.

The preferred first and the second embodiments of the present invention are described above. However, the present invention should not be limited to these embodiments. For example, as described below, various improvements and design changes are possible without departing from the spirit of the present invention.

Figure 2:
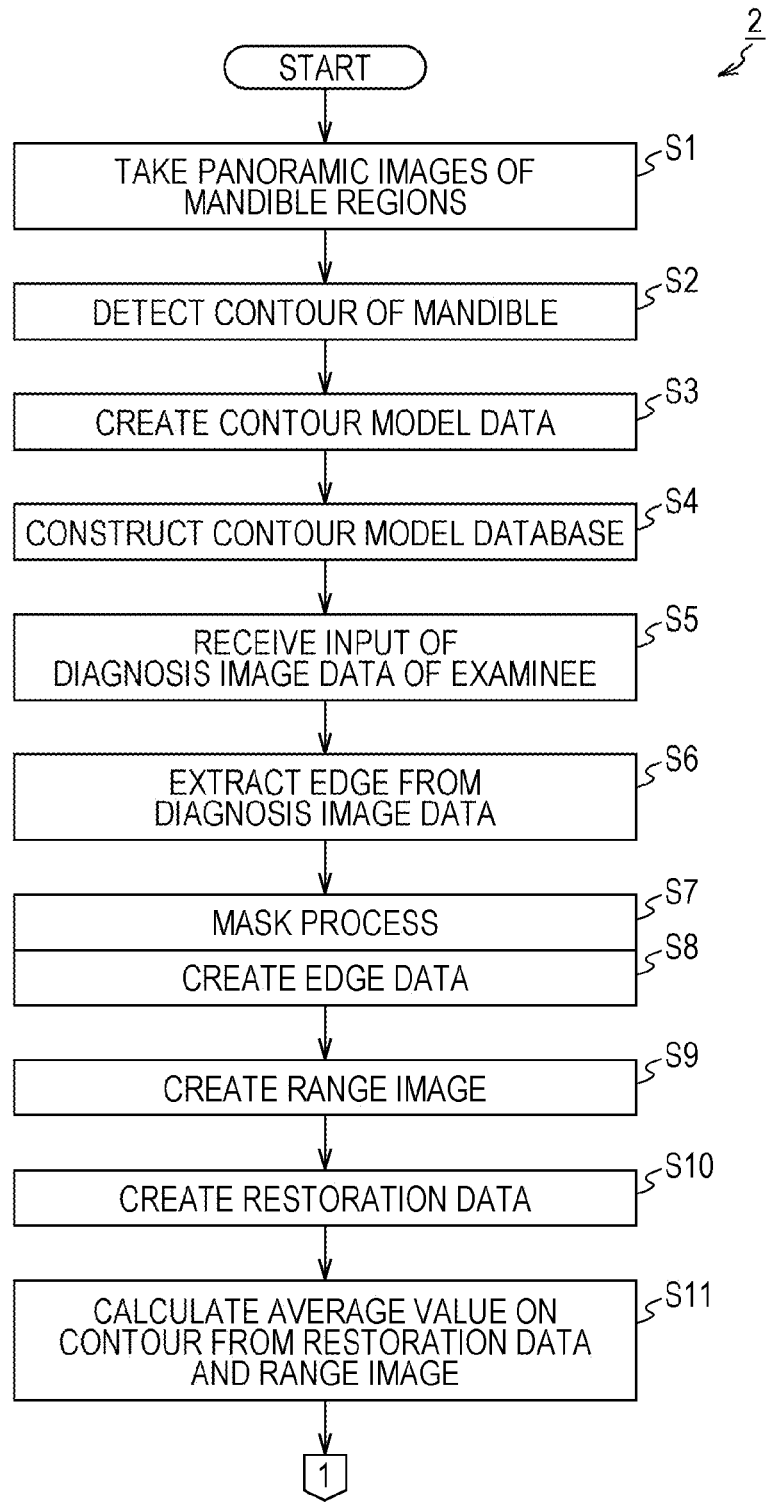
FIG. 2 is a flowchart illustrating a flow of processes by the diagnosis support computer according to the first embodiment.
Figure 3:
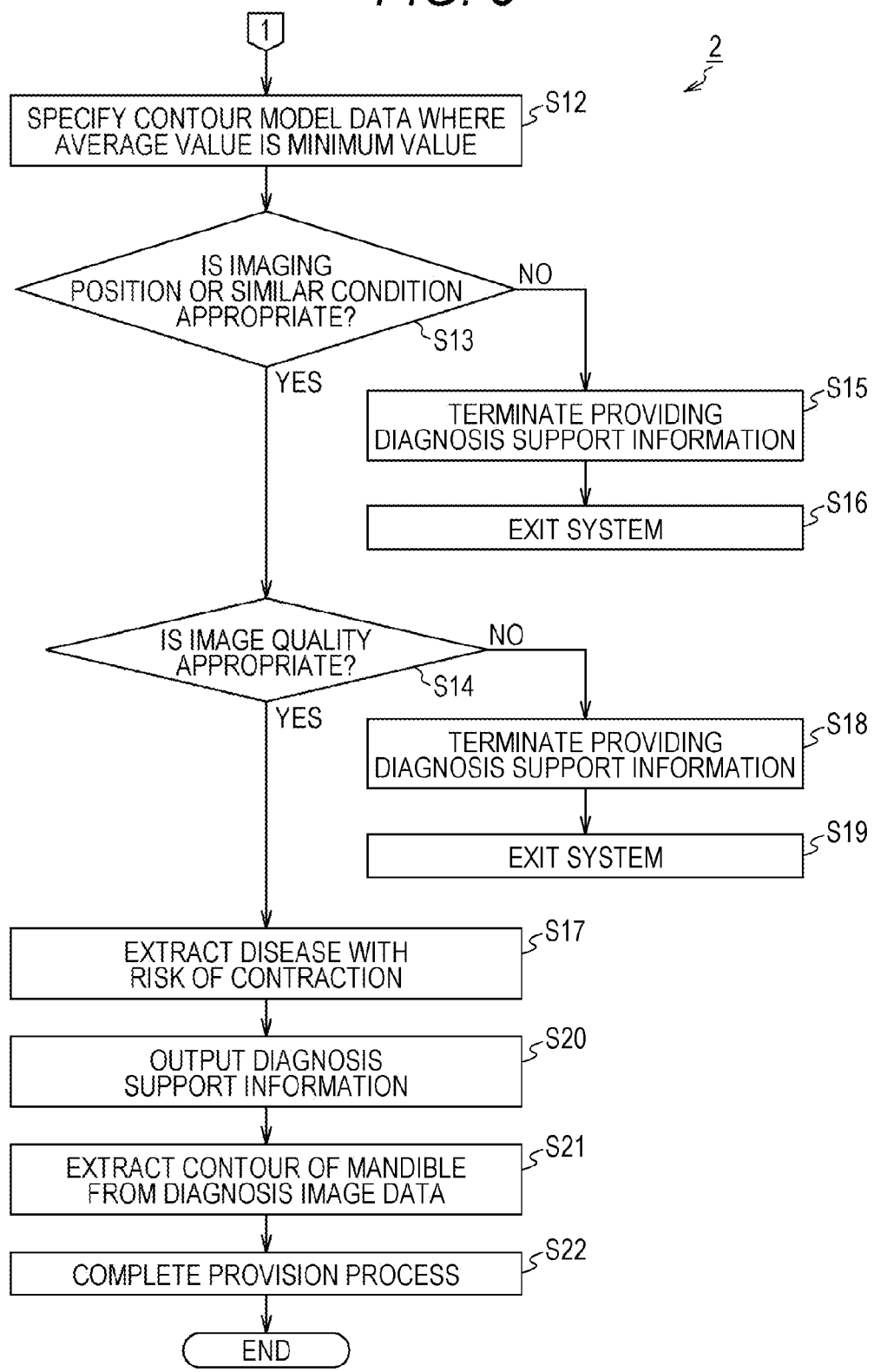
FIG. 3 is a flowchart illustrating the flow of processes by the diagnosis support computer according to the first embodiment.
Figure 5:
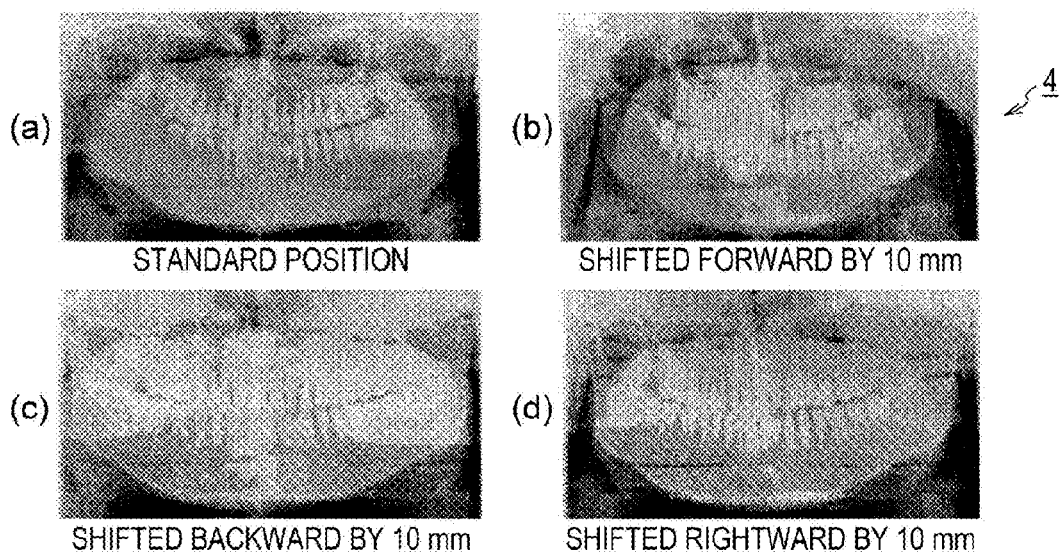
FIG. 5(a) is an explanatory view illustrating an exemplary panoramic radiograph taken under appropriate radiographic imaging conditions.
FIG. 5(b) is an explanatory view illustrating an exemplary panoramic radiograph taken shifted forward by 10 mm (inappropriate radiographic imaging condition)
FIG. 5(c) is an explanatory view illustrating an exemplary panoramic radiograph taken shifted backward by 10 mm (inappropriate radiographic imaging condition)
FIG. 5(d) is an explanatory view illustrating an exemplary panoramic radiograph taken shifted rightward by 10 mm (inappropriate radiographic imaging condition).
Figure 6:
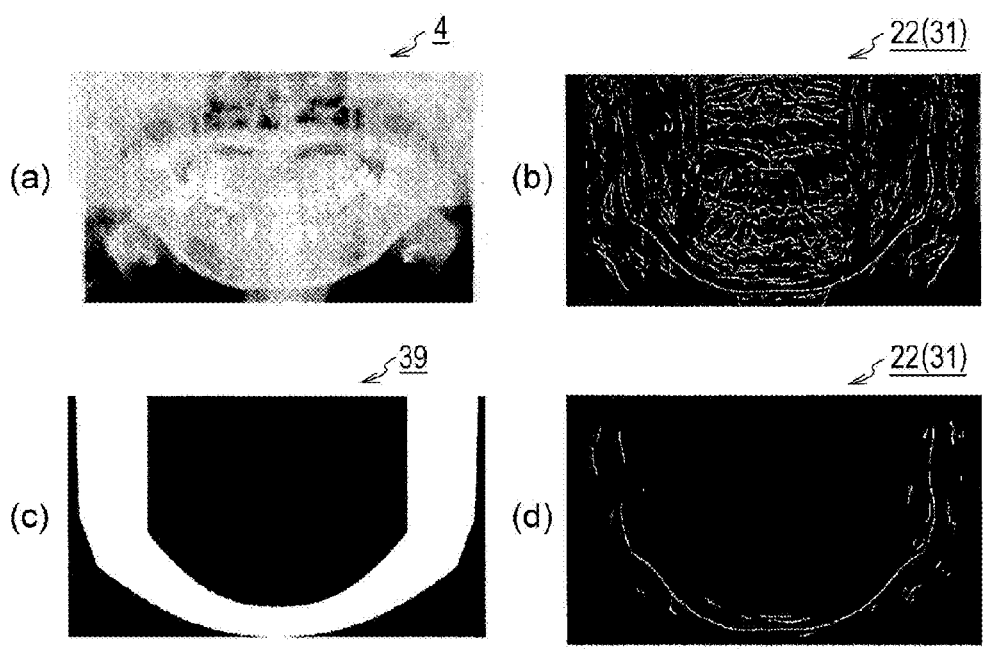
FIG. 6(a) is a panoramic radiograph of a subject of diagnostic support.
FIG. 6(b) is an explanatory view illustrating edge data.
FIG. 6(c) is an explanatory view illustrating a mask pattern.
FIG. 6(d) is an explanatory view illustrating edge data after a mask process.

That is, in the diagnosis support system 1 according to the first embodiment, a flow of processes by the diagnosis support computer 3 is described based on the flowcharts in FIG. 2 and FIG. 3. In the diagnosis support system 101 according to the second embodiment, a flow of processes by the diagnosis support computer 103 is described based on the flowcharts in FIG. 12 and FIG. 13. However, the flow of the processes is not limited to these. In the diagnosis support system 1 according to the first embodiment, for example, construction of the contour model database 19 and the subsequent process, such as a process of judgment for appropriateness, need not to be performed consecutively. Alternatively, a judgment process of imaging condition such as an imaging position and a judgment process of image quality such as a density profile may be performed simultaneously. Alternatively, these judgment processes may be performed in reverse order. In first and the second embodiments, various well-known image analysis techniques are employed in creation of the edge data 22 and searching for the similar contour model data 15. However, these methods should not be limited. The edge data 22 or similar data and the contour shape may be specified using other image analysis techniques and image analysis methods.

The diagnosis support system 101 according to the second embodiment shows combination of the Canny filter and the Kirsch method as an image analysis technique for the edge data extraction unit 130 where the edge data 129 is extracted from the mandible/maxillary sinus diagnosis image data 116. However, this should not be construed in a limiting sense. The edge data 129 may be extracted using another image analysis technique. In first and the second embodiments, the atlases 114 of the maxillary sinuses are created and the region of interest 115 is specified using the plurality of similar reference model data 113 found by the similarity search. However, this should not be construed in a limiting sense. Only one of the similar reference model data 113 inferred to be the highest degree of similarity may be used.

CITATION LIST

Patent Literatures

Patent Document 1: JP-A-2008-36068
Patent Document 2: Japanese Patent No. 3964795
Patent Document 3: WO 2006/043523 A Non Patent Literatures Non-Patent Document 1: Hara T, Mori S, Kaneda T, Hayashi T, Katsumata A, Fujita H, "Automated contralateral subtraction of dental panoramic radiographs for detecting abnormalities in paranasal sinus", Proc. of SPIE, 2011, Vol. 7963, p. 79632R-1-79632R-6
Non-Patent Document 2: Guimond A, Meunier J, Thirion J P, "Average Brain Models: A Convergence Study", Computer Vision and Image Understanding, 2000, Vol. 77, p. 192-210
Non-Patent Document 3: Dinov I D, Mega M S, Thompson P M, Lee L, Woods R P, Holmes C J, Sumners D W, Toga A W, "Analyzing Functional Brain Images in a Probabilistic Atlas; A Validation of Subvolume Thresholding", Journal of Computer Assisted Tomography, 2000, Vol. 24(1), p. 128-138
Non-Patent Document 4: Park H, Bland P H, Meyer C R, "Construction of an Abdominal Probabilistic Atlas and its Application in Segmentation", IEEE TRANSACTIONS ON MEDICAL IMAGING, 2003, Vol. 22(4), p. 483-492
Non-Patent Document 5: Teruhiko KITAGAWA, Xiangrong ZHOU, Takeshi HARA, Hiroshi FUJITA, Ryujiro YOKOYAMA, Hiroshi KONDO, Masayuki KANEMATSU, Hiroaki HOSHI "Generation of a Probabilistic Liver Atlas and Its Application to Automated Liver Segmentation Method in Non-contrast X-Ray Torso CT Images" IEICE TRANSACTIONS D, 2008, Vol. J91-D (7), p. 1837-1850
Non-Patent Document 6: Blezek D J, Miller J V, "Atlas stratification", Medical Image Analysis, 2007, Vol. 11, p. 443-457
Non-Patent Document 7: Canny J F, "A Computational Approach Edge Detection", IEEE TRANSACTION ON PATTERN ANALYSIS AND MACHINE INTELLIGENCE, 1986, VOL. PAMI-8(6), p. 679-698
Non-Patent Document 8: Zeyu Zheng and other three, "Quantitative Evaluation of Partial Shape Characteristics of Petal in Sacred Lotus Based on P-type Fourier Descriptors" Breeding Research, 2005, 7(3), p 133-142
Non-Patent Document 9: Kirsch R, "Computer Determination of the Constituent Structure of Biological Images", COMPUTERS AND BIOMEDICAL RESEARCH, 1971, Vol. 4, p. 315-328
Non-Patent Document 10: Takuya MATSUMOTO and other eight, "Fundamental Study on Thickness Measurement of Mandible Cortical Bone in Dental Panoramic Radiographs", JAMIT Annual Meeting 2010, Proceedings CD-ROM, 2010, p. 3-11
Non-Patent Document 11: Tatsuro HAYASHI and other seven, "Development of Method of Automated Detection of Calcification in Carotid Artery Using Top-Hat Filter on Dental Panoramic Radiographs", The 15th Congress of Clinical Imaging for Oral and Maxillofacial Lesions 2010, O-S5-16, p. 47

The invention claimed is:
1. A diagnosis support computer comprising:
a model data acquisition unit configured to receive an input of panoramic radiographs of a mandible region of a provider of mandible model, which are taken for each of a plurality of radiographic imaging conditions including an appropriate radiographic imaging condition and an inappropriate radiographic imaging condition, the appropriate/inappropriate radiographic imaging condition being determined by a position judgment unit and an image quality judgment unit, the appropriate radiographic imaging condition being a condition in which, when taking the panoramic image of a mandible region, positioning of a median line to the center of the face of the provider of mandible model and an image quality are adjusted, the panoramic image obtained has no skewing, deformation, and image quality error, the inappropriate radiographic imaging condition being either a condition in which the panoramic image is taken at an incorrect position where the position or the orientation of the mandible region and an imaging posture of the provider of mandible model are out of appropriate range or a condition in which the panoramic image is taken where ray dose is insufficient or too much or the image quality is inappropriate, and obtain a plurality of mandible model data from the panoramic radiographs;
a contour model creation unit configured to extract a contour of the mandible from the obtained mandible model data to create contour model data;
a contour database storage unit configured to store the created contour model data together with imaging information on an imaging position, an imaging posture, and an image quality, and provider information including an age, a gender, and a disease history of the provider of mandible model, the contour database storage unit constructing contour model database;
a diagnosis image data receiving unit configured to receive an input of diagnosis image data, the diagnosis image data being obtained by taking a panoramic radiograph of a mandible region of an examinee who is a subject of diagnostic support;
an edge extraction unit configured to extract edge data of the mandible from the received diagnosis image data;
a similar model searching unit configured to collate the extracted edge data and a plurality of contour model data of the contour model database to search for the similar contour model data;
the position judgment unit configured to judge an imaging position of the diagnosis image data and appropriateness of a position of an imaging posture based on the imaging information on the contour model data found by the similarity search;
the image quality judgment unit configured to judge degree of appropriateness of image quality including a density profile and a contrast of the diagnosis image data based on the imaging information of the contour model data found by the similarity search; and
a diagnosis support information provision unit configured to provide a disease with a risk of contraction as the diagnosis support information based on the provider information of the contour model data found by the similarity search, the diagnosis support information being provided with respect to the diagnosis image data judged to be taken under the appropriate imaging conditions by the position judgment unit and the image quality judgment unit.

2. The diagnosis support computer according to claim 1, further comprising:
a mandible contour detection unit configured to detect a contour of the mandible included in the diagnosis image data; and
a disease detection supporting unit configured to provide information to allow a doctor to detect at least one disease of osteoporosis, calcification in carotid artery, and maxillary sinusitis based on the diagnosis contour data of the detected contour of the mandible.

3. The diagnosis support computer according to claim 1, wherein
the similar model searching unit further includes:
a range image creation unit configured to create a range image drawn by changing shading according to a distance from the edge of the mandible, using the extracted edge data;
a contour restoration unit configured to create a contour restoration shape data of the mandible from the contour model data, the contour restoration shape data being made from the obtained mandible model data from which the contour of the mandible is not yet extracted by the contour model creation unit;
an average value calculation unit configured to superimpose restoration data of the restored contour shape and range image data of the created range image, the average value calculation unit calculating an average value on a contour; and
a contour model specification unit configured to specify the contour model data with a contour shape of the mandible where the calculated average value is a minimum value, the contour model specification unit determining the specified contour model data as the similar contour model data.

4. The diagnosis support computer according to claim 2, wherein
the model data acquisition unit further includes an image data acquisition unit configured to obtain panoramic image data of the panoramic radiograph where regions including the mandible region and the maxillary sinus region of the provider of mandible model have been taken as a subject to be imaged, the image data acquisition unit storing the panoramic image data,
the diagnosis image data receiving unit further includes a mandible/maxillary sinus diagnosis image data receiving unit configured to receive an input of mandible/maxillary sinus diagnosis image data of a test object image, the test object image being taken as the panoramic radiograph including regions of the mandible and the maxillary sinus of an examinee to be diagnosed,
the edge extraction unit further includes an edge data extraction unit configured to extract edge data candidate for a contour of the mandible from the received mandible/maxillary sinus diagnosis image data using a digital analysis technique, and
the similar model searching unit further includes a mandible similar model searching unit configured to collate the extracted edge data and a plurality of reference model data stored in the model database to search for similar reference model data with a contour shape of the mandible similar to the edge data, wherein
the diagnosis support computer further includes
a reference model data creation unit configured to specify a contour shape of the mandible and a position of the maxillary sinus from the panoramic image data to create reference model data,
a reference database construction unit configured to store a plurality of the created reference model data, the reference database construction unit constructing model database,
an atlas creation unit configured to extract a region of a position of the maxillary sinus from the similar reference model data found by the similarity search to create an atlas of the maxillary sinus,
a maxillary sinus image extraction unit configured to extract a maxillary sinus image corresponding to a region of the maxillary sinus from the mandible/maxillary sinus diagnosis image data based on the atlas,
a feature quantity calculation unit configured to calculate each of feature quantities of the extracted right and left pair of maxillary sinus image, and
a risk rate estimation unit configured to estimate a risk rate associated with a contraction of odontogenic maxillary sinusitis by the examinee, the mandible/maxillary sinus diagnosis image data being obtained from the examinee, the risk rate being estimated from feature quantity data associated with the calculated feature quantities.

5. The diagnosis support computer according to claim 4, wherein the feature quantities correspond to a mean value, a median, a mode, a standard deviation, a histogram distribution of pixels constituting the regions of maxillary sinuses, and the size of the region.

6. The diagnosis support computer according to claim 4, wherein
the edge data extraction unit further includes:
a smoothing unit configured to perform a smoothing process on the mandible/maxillary sinus diagnosis image data using a Gaussian filter, the smoothing unit removing noise included in the mandible/maxillary sinus diagnosis image data;
a mask unit configured to preliminary perform a mask process on a position where presence of the mandible is expected in the obtained smoothed data;
a gradient direction prediction unit configured to predict a gradient direction of an edge constituting a contour shape of the mandible in the obtained mask data;
a gradient intensity calculation unit configured to calculate gradient and intensity of the edge of the obtained gradient prediction data using a Kirsch method;
a thinning unit configured to thin the edge of the calculated intensity data by non-maximum suppression process; and
a threshold process unit configured to perform a hysteresis threshold process on the obtained thinned data to extract the edge data.

7. The diagnosis support computer according to claim 4, wherein
the mandible similar model searching unit further includes:
a distance transform unit configured to create a distance transform image from the edge data extracted from the mandible/maxillary sinus diagnosis image data;
an affine transformation unit configured to perform an affine transformation process on the reference model data stored in the model database; and
a similarity degree estimation unit configured to estimate a degree of similarity between distance transform image data of the distance transform image and the reference model data after an affine transformation process, and extract similar reference model.

8. The diagnosis support computer according to claim 1, wherein a head phantom made by artificial bones for radiographic imaging is used as a part of the provider of mandible models.

9. A non-transitory program storage medium storing a diagnosis support program for allowing a diagnosis support computer to function as:
a model data acquisition unit configured to receive an input of panoramic radiographs of a mandible region of a provider of mandible model, which are taken for each of a plurality of radiographic imaging conditions including an appropriate radiographic imaging condition and an inappropriate radiographic imaging condition, the appropriate/inappropriate radiographic imaging condition being determined by a position judgment unit and an image quality judgment unit, the appropriate radiographic imaging condition being a condition in which, when taking the panoramic image of a mandible region, positioning of a median line to the center of the face of the provider of mandible model and an image quality are adjusted, the panoramic image obtained has no skewing, deformation, and image quality error, the inappropriate radiographic imaging condition being either a condition in which the panoramic image is taken at an incorrect position where the position or the orientation of the mandible region and an imaging posture of the provider of mandible model are out of appropriate range or a condition in which the panoramic image is taken where ray dose is insufficient or too much or the image quality is inappropriate, and obtain a plurality of mandible model data from the panoramic radiographs;
a contour model creation unit configured to extract a contour of the mandible from the obtained mandible model data to create contour model data;
a contour database storage unit configured to store the created contour model data together with imaging information on an imaging position, an imaging posture, and an image quality, and provider information including an age, a gender, and a disease history of the provider of mandible model, the contour database storage unit constructing contour model database;
a diagnosis image data receiving unit configured to receive an input of diagnosis image data, the diagnosis image data being obtained by taking a panoramic radiograph of a mandible region of an examinee who is a subject of diagnostic support;
an edge extraction unit configured to extract edge data of the mandible from the received diagnosis image data;
a similar model searching unit configured to collate the extracted edge data and a plurality of contour model data of the contour model database to search for the similar contour model data;
the position judgment unit configured to judge an imaging position of the diagnosis image data and appropriateness of a position of an imaging posture based on the imaging information on the contour model data found by the similarity search;
the image quality judgment unit configured to judge degree of appropriateness of image quality including a density profile and a contrast of the diagnosis image data based on the imaging information of the contour model data found by the similarity search; and
a diagnosis support information provision unit configured to provide a disease with a risk of contraction as the diagnosis support information based on the provider information of the contour model data found by the similarity search, the diagnosis support information being provided with respect to the diagnosis image data judged to be taken under the appropriate imaging conditions by the position judgment unit and the image quality judgment unit.

10. The non-transitory program storage medium according to claim 9, wherein
the diagnosis support program allows the diagnosis support computer to further function as:
a mandible contour detection unit configured to detect a contour of the mandible included in the diagnosis image data; and
a disease detection supporting unit configured to provide information to allow a doctor to detect at least one disease of osteoporosis, calcification in carotid artery, and maxillary sinusitis based on the diagnosis contour data of the detected contour of the mandible.

11. The non-transitory program storage medium according to claim 9, wherein
the diagnosis support program allows the diagnosis support computer to further function as:

a range image creation unit configured to create a range image drawn by changing shading according to a distance from the edge of the mandible, using the extracted edge data;

a contour restoration unit configured to create a contour restoration shape data of the mandible from the contour model data, the contour restoration shape data being made from the obtained mandible model data from which the contour of the mandible is not yet extracted by the contour model creation unit;

an average value calculation unit configured to superimpose restoration data of the restored contour shape and range image data of the created range image, the average value calculation unit calculating an average value on a contour; and a contour model specification unit configured to specify the contour model data with a contour shape of the mandible where the calculated average value is a minimum value, the contour model specification unit determining the specified contour model data as the similar contour model data.

12. The non-transitory program storage medium according to claim 9, wherein
the diagnosis support program allows the diagnosis support computer to further function as:
the model data acquisition unit that includes an image data acquisition unit configured to obtain panoramic image data of the panoramic radiograph where regions including the mandible region and the maxillary sinus region of the provider of mandible model have been taken as a subject to be imaged, the image data acquisition unit storing the panoramic image data;
the diagnosis image data receiving unit that includes a mandible/maxillary sinus diagnosis image data receiving unit configured to receive an input of mandible/maxillary sinus diagnosis image data of a test object image, the test object image being taken as the panoramic radiograph including regions of the mandible and the maxillary sinus of an examinee to be diagnosed;
the edge extraction unit that includes an edge data extraction unit configured to extract edge data candidate for a contour of the mandible from the received mandible/maxillary sinus diagnosis image data using a digital analysis technique, and
the similar model searching unit that includes a mandible similar model searching unit configured to collate the extracted edge data and a plurality of reference model data stored in the model database to search for similar reference model data with a contour shape of the mandible similar to the edge data;
a reference model data creation unit configured to specify a contour shape of the mandible and a position of the maxillary sinus from the panoramic image data to create reference model data;
a reference database construction unit configured to store a plurality of the created reference model data, the reference database construction unit constructing model database;
an atlas creation unit configured to extract a region of a position of the maxillary sinus from the similar reference model data found by the similarity search to create an atlas of the maxillary sinus;
a maxillary sinus image extraction unit configured to extract a maxillary sinus image corresponding to a region of the maxillary sinus from the mandible/maxillary sinus diagnosis image data based on the atlas;
a feature quantity calculation unit configured to calculate each of feature quantities of the extracted right and left pair of maxillary sinus image; and
a risk rate estimation unit configured to estimate a risk rate associated with a contraction of odontogenic maxillary sinusitis by the examinee, the mandible/maxillary sinus diagnosis image data being obtained from the examinee, the risk rate being estimated from feature quantity data associated with the calculated feature quantities.

13. The non-transitory program storage medium according to claim 11, wherein the feature quantities correspond to a mean value, a median, a mode, a standard deviation, a histogram distribution of pixels constituting the regions of maxillary sinuses, and the size of the region.

14. The non-transitory program storage medium according to claim 12, wherein
the diagnosis support program allows the diagnosis support computer to further function as the edge data extraction unit further including:
a smoothing unit configured to perform a smoothing process on the mandible/maxillary sinus diagnosis image data using a Gaussian filter, the smoothing unit removing noise included in the mandible/maxillary sinus diagnosis image data;
a mask unit configured to preliminary perform a mask process on a position where presence of the mandible is expected in the obtained smoothed data;
a gradient direction prediction unit configured to predict a gradient direction of an edge constituting a contour shape of the mandible in the obtained mask data;
a gradient intensity calculation unit configured to calculate gradient and intensity of the edge of the obtained gradient prediction data using a Kirsch method;
a thinning unit configured to thin the edge of the calculated intensity data by non-maximum suppression process; and
a threshold process unit configured to perform a hysteresis threshold process on the obtained thinned data to extract the edge data.

15. The non-transitory program storage medium according to claim 12, wherein
the diagnosis support program allows the diagnosis support computer to further function as the mandible similar model searching unit further including:
a distance transform unit configured to create a distance transform image from the edge data extracted from the diagnosis image data;
an affine transformation unit configured to perform an affine transformation process on the reference model data stored in the model database; and
a similarity degree estimation unit configured to estimate a degree of similarity between distance transform image data of the distance transform image and the reference model data after an affine transformation process, and extract similar reference model.

16. The non-transitory program storage medium according to claim 9, wherein the program storage medium is at least one of a central processing unit (CPU), a memory, and a hard disk drive, which are mounted to the diagnosis support computer.

17. A diagnosis support system including the diagnosis support computer according to claim 1 for analyzing input panoramic radiographs using the diagnosis support computer.

* * * * *